(12) United States Patent
Friedenberg et al.

(10) Patent No.: US 12,161,864 B2
(45) Date of Patent: Dec. 10, 2024

(54) CALIBRATION OF ELECTRODE-TO-MUSCLE MAPPING FOR FUNCTIONAL ELECTRICAL STIMULATION

(71) Applicant: Battelle Memorial Institute, Columbus, OH (US)

(72) Inventors: David A. Friedenberg, Worthington, OH (US); Po-Hsu Chen, Dublin, OH (US); Samuel Colachis, Columbus, OH (US); Nicholas Annetta, Columbus, OH (US); Douglas E. Boyd, Columbus, OH (US); Collin Dunlap, Columbus, OH (US); Ian W. Baumgart, Columbus, OH (US); Herbert S. Bresler, Bexley, OH (US)

(73) Assignee: BATTELLE MEMORIAL INSTITUTE, Columbus, OH (US)

(*) Notice: Subject to any disclaimer, the term of this patent is extended or adjusted under 35 U.S.C. 154(b) by 0 days.

(21) Appl. No.: 18/390,797

(22) Filed: Dec. 20, 2023

(65) Prior Publication Data

US 2024/0123222 A1 Apr. 18, 2024

Related U.S. Application Data

(63) Continuation of application No. 17/969,896, filed on Oct. 20, 2022, now Pat. No. 11,883,656, which is a
(Continued)

(51) Int. Cl.
*A61N 1/36* (2006.01)
*A61N 1/02* (2006.01)
(Continued)

(52) U.S. Cl.
CPC ........ *A61N 1/36003* (2013.01); *A61N 1/025* (2013.01); *A61N 1/08* (2013.01);
(Continued)

(58) Field of Classification Search
CPC ....... A61N 1/36003; A61N 1/025; A61N 1/08
(Continued)

(56) References Cited

U.S. PATENT DOCUMENTS

2012/0059432 A1  3/2012 Emborg et al.
2013/0066395 A1  3/2013 Simon et al.
(Continued)

*Primary Examiner* — Nadia A Mahmood
(74) *Attorney, Agent, or Firm* — Lippes Mathias LLP

(57) ABSTRACT

A functional electrical stimulation (FES) device includes electrodes arranged to apply functional electrical stimulation to a body part of the user. FES stimulation is performed by: receiving values of a set of user metrics for the user; receiving a target position of the body part represented as values for a set of body part position measurements; determining a user-specific energization pattern for producing the target position based on the received target position and the received values of the set of user metrics for the user; and energizing the electrodes of the FES device in accordance with the determined user-specific energization pattern. The determination may utilize an FES calibration database with records having fields containing: values of the set of user metrics for reference users; energization patterns; and values of the set of body part position metrics for positions assumed by the body part in response to applying the energization patterns.

14 Claims, 13 Drawing Sheets

Related U.S. Application Data continuation of application No. 17/575,084, filed on Jan. 13, 2022, now Pat. No. 11,504,531, which is a continuation of application No. 17/320,604, filed on May 14, 2021, now Pat. No. 1,126,833.

(60) Provisional application No. 63/058,914, filed on Jul. 30, 2020, provisional application No. 63/058,786, filed on Jul. 30, 2020, provisional application No. 63/024,589, filed on May 14, 2020.

(51) Int. Cl.
*A61N 1/08* (2006.01)
*G06N 20/00* (2019.01)
*G16H 20/30* (2018.01)
*A61B 5/397* (2021.01)

(52) U.S. Cl.
CPC ............. *G06N 20/00* (2019.01); *G16H 20/30* (2018.01); *A61B 5/397* (2021.01)

(58) Field of Classification Search
USPC .......................................................... 607/48
See application file for complete search history.

(56) References Cited

U.S. PATENT DOCUMENTS

| | | |
|---|---|---|
| 2016/0361543 A1 | 12/2016 | Kaula et al. |
| 2017/0157396 A1 | 6/2017 | Dixon et al. |
| 2017/0303849 A1* | 10/2017 | De Sapio ............. A61B 5/4023 |
| 2019/0247650 A1 | 8/2019 | Tran |

* cited by examiner

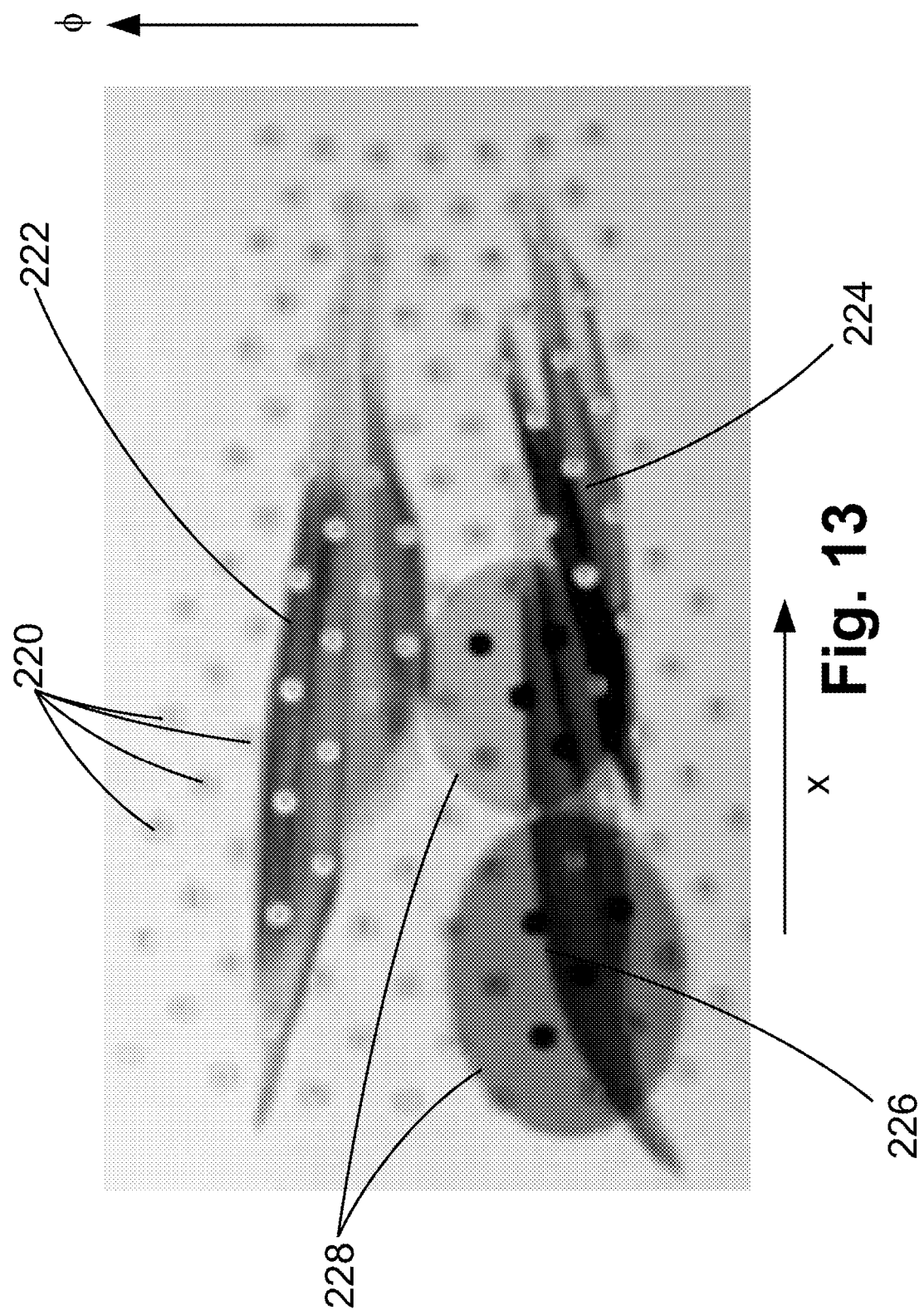

CALIBRATION OF ELECTRODE-TO-MUSCLE MAPPING FOR FUNCTIONAL ELECTRICAL STIMULATION

This application is a Continuation of U.S. Ser. No. 17/969,896 filed Oct. 20, 2022 and now issued as U.S. Pat. No. 11,883,656 which is a Continuation of U.S. Ser. No. 17/575,084 filed Jan. 13, 2022 and now issued as U.S. Pat. No. 11,504,531 which is a Continuation of U.S. Ser. No. 17/320,604 filed May 14, 2021 and titled "CALIBRATION OF ELECTRODE-TO-MUSCLE MAPPING FOR FUNCTIONAL ELECTRICAL STIMULATION" and now issued as U.S. Pat. No. 11,266,833 which claims the benefit of U.S. Provisional Application No. 63/024,589 filed May 14, 2020 and titled "CALIBRATION OF ELECTRODE-TO-MUSCLE MAPPING FOR FUNCTIONAL ELECTRICAL STIMULATION" and which claims the benefit of U.S. Provisional Application No. 63/058,786 filed Jul. 30, 2020 and titled "CALIBRATION OF ELECTRODE-TO-MUSCLE MAPPING FOR FUNCTIONAL ELECTRICAL STIMULATION" and which claims the benefit of U.S. Provisional Application No. 63/058,914 filed Jul. 30, 2020 and titled "FUNCTIONAL ELECTRICAL STIMULATION CALIBRATION SYSTEMS, DEVICES, AND METHODS".

U.S. Provisional Application No. 63/024,589 filed May 14, 2020 and titled "CALIBRATION OF ELECTRODE-TO-MUSCLE MAPPING FOR FUNCTIONAL ELECTRICAL STIMULATION" is incorporated herein by reference in its entirety.

U.S. Provisional Application No. 63/058,786 filed Jul. 30, 2020 and titled "CALIBRATION OF ELECTRODE-TO-MUSCLE MAPPING FOR FUNCTIONAL ELECTRICAL STIMULATION" is incorporated herein by reference in its entirety.

U.S. Provisional Application No. 63/058,914 filed Jul. 30, 2020 and titled "FUNCTIONAL ELECTRICAL STIMULATION CALIBRATION SYSTEMS, DEVICES, AND METHODS" is incorporated herein by reference in its entirety.

BACKGROUND

The following relates to the functional electrical stimulation (FES) arts, to calibration of FES devices, to rehabilitative or assistive systems employing FES devices, and to related arts.

U.S. Pub. No. 2018/0154133 A1 published Jun. 7, 2018 and filed Jan. 16, 2018, titled "Neural Sleeve for Neuromuscular Stimulation, Sensing and Recording" is incorporated herein by reference in its entirety, and provides some nonlimiting illustrative examples of FES devices suitably used in FES systems disclosed herein.

Functional electrical stimulation (FES) is a type of neuromuscular electrical stimulation (NMES) in which functional activity (movement) of muscles is enhanced by, or in the case of complete paralysis wholly driven by, the applied NMES. A system typically includes an FES device with electrodes that contact the skin. Alternatively, transcutaneous electrodes can be used. By way of illustration, the FES device may be a glove worn on a paralyzed hand, or a sleeve worn on a paralyzed arm or leg, and/or so forth; in which the glove or sleeve or so forth has an array of electrodes disposed on the inside that contact the skin of the hand or limb on which the glove or sleeve is placed.

The FES device is controlled by command signals that indicate intended movements of the body part. These command signals can be generated by the person wearing the FES device in various ways. In one approach, an associated computer displays a graphical user interface (GUI) presenting various icons representing various movements. The wearer stares at a particular icon, which action is detected by a gaze tracking system, and the computer generates the intended movement command corresponding to the particular icon. In another approach, a brain-computer interface (BCI) monitors electrical activity of the brain, and a computer is programmed to decode the electrical activity to determine the intended movement when the wearer mentally visualizes or wills that intended movement. In another approach, the FES device also includes electrodes (which may be the same as the stimulation electrodes or a different set of electrodes) that detect electromyography (EMG) signals generated by the muscles themselves in response to the wearer willing the intended movement, and the EMG signals are decoded by a computer to generate the intended movement command. (In these systems, the EMG signals are not sufficient by themselves to cause the intended movement, for example due to a spinal cord injury attenuating the communication from the brain or due to limitations on autonomous movement control due to a stroke).

The command signal (however sourced) is then converted to an electrode energization pattern that is effective to cause the muscles to contract in a manner that implements the movement indicated by the command signal. The electrode energization pattern for the electrodes specifies one or more energization parameters for each electrode, such as parameters indicating: whether the electrode is energized; applied voltage magnitude; applied voltage frequency; applied voltage waveform shape; various combinations thereof; or so forth. An FES driver then applies the electrode energization pattern to the electrodes of the FES device to generate the movement.

A difficulty in such a system is efficiently determining the electrode energization patterns that effectively produce the desired movements. This is challenging for various reasons. For example, the electrode energization pattern for producing a particular movement usually is different for different individuals, due to factors such as individual variations in anatomy (including underlying muscle anatomy), individual variations in skin electrical conductivity over the body part (which impacts how effectively a given voltage at a given electrode energizes the underlying muscle), individual variations in how the FES device is worn (which impacts electrode-muscle coupling), and so forth. Even for a given individual, the electrode energization pattern may need to be redetermined frequently, due to factors such as day-to-day variation in positioning of the FES device on the body part, day-to-day variation in skin electrical conductivity, or so forth. Still further, for a practical FES system it is usually desirable to provide multiple movements. For example, a number of different hand and arm movements are needed to perform a single task such as brushing teeth; and, the user may want to be able to perform multiple tasks such as brushing teeth and combing hair.

A usual approach for determining the electrode energization patterns for producing the desired movements is a tedious, manually intensive process in which multiple parameters including electrode location, amplitude, and stimulation frequency are adjusted by a trained physical therapist to evoke each desired movement. This calibration approach also limits the possibility of the wearer using the device at home without the assistance of a physical therapist. The need for a physical therapist to calibrate the system on a daily or other frequent basis is problematic, especially for FES systems whose goal is to enhance autonomy of the user using the FES device.

While the foregoing relates to clinical applications, it is noted that FES may also be usefully applied in other contexts, such as gaming, virtual reality (VR) systems, or augmented reality (AR) systems. For example, in a gaming or VR environment, FES may be applied to simulate an external force applied to the user, e.g. recoil when firing a gun or the force of a punch or other impact to the body. In an illustrative AR context, FES may be applied to cause the user to assume a specific position, for example, a hand grip on a golf club in an AR system used for training a golfer.

Disclosed herein are certain improvements.

BRIEF SUMMARY

In accordance with some illustrative embodiments disclosed herein, a functional electrical stimulation (FES) system is disclosed. An FES device is configured for connection with an associated body part and includes electrodes arranged to apply functional electrical stimulation to the associated body part and further includes sensors to measure a position of the associated body part. An electronic processor is programmed to perform an iterative calibration method to determine a calibrated electrode energization pattern for producing a movement of the associated body part. An iteration of the iterative calibration method includes: for each proposal of a current pool of proposals, applying the proposal comprising an electrode energization pattern to the electrodes of the FES device and receiving sensor readings from the sensors of the FES device with the associated body part positioned by the applying of the proposal and generating an error metric for the proposal with respect to the movement using an error function corresponding to the movement that depends on the sensor readings; and generating an updated pool of proposals for a next iteration of the iterative calibration method by modifying the proposals of the current pool of proposals based on the generated error metrics. The iterative calibration method selects, based on the error metrics, the calibrated electrode energization pattern for producing the movement from the proposals applied during one or more iterations of the iterative calibration method.

In accordance with some illustrative embodiments disclosed herein, a non-transitory storage medium stores instructions readable and executable by an electronic processor in operative communication with an FES device configured for connection with an associated body part and including electrodes arranged to apply functional electrical stimulation to the associated body part. The instructions are readable and executable by the electronic processor to perform a calibration method to determine a calibrated electrode energization pattern for producing a movement of the associated body part. The calibration method includes: applying a candidate electrode energization pattern to the electrodes of the FES device by ramping up an amplitude of the electrode energization pattern applied to the electrodes of the FES device; and stopping the ramping in response to the first to occur of (i) the amplitude reaching a maximum amplitude or (ii) receiving a user-generated stop signal.

In accordance with some illustrative embodiments disclosed herein, an FES system comprises: an FES device configured for connection with an associated body part and including electrodes arranged to apply functional electrical stimulation to the associated body part and further including sensors to measure a position of the associated body part; and an electronic processor programmed to perform an iterative calibration method to determine calibrated electrode energization patterns for producing a plurality of different movements of the associated body part. An iteration of the iterative calibration method includes: for each proposal of a current pool of proposals, applying the proposal comprising an electrode energization pattern to the electrodes of the FES device and receiving sensor readings from the sensors of the FES device with the associated body part positioned by the applying of the proposal; for each movement of the plurality of different movements, generating an error metric for the proposal with respect to the movement using an error function corresponding to the movement that is functionally dependent on the sensor readings; for each movement of the plurality of different movements, generating a movement-specific pool of proposals by modifying the proposals of the current pool of proposals based on the generated error metrics for the movement; and combining the movement-specific pools of proposals for the plurality of different movements to generate an updated pool of proposals for a next iteration of the iterative calibration method.

In accordance with some illustrative embodiments disclosed herein, an FES system comprises an FES device configured for connection with an associated body part of a user and including electrodes arranged to apply functional electrical stimulation to the associated body part of the user, and an electronic processor programmed to perform FES stimulation by operations including: receiving values of a set of user metrics for the user; receiving a target position of the associated body part represented as values for a set of body part position measurements; determining a user-specific energization pattern for producing the target position based on the received target position and the received values of the set of user metrics for the user; and energizing the electrodes of the FES device in accordance with the determined user-specific energization pattern. In some such embodiments, the determining of the user-specific energization pattern includes determining the user-specific energization pattern based on a comparison of (i) the received target movement and the received values of the set of user metrics for the user and (ii) records stored in an FES calibration database, where each record of the FES calibration database includes fields containing values of the set of user metrics for a reference user and values of the set of body part position metrics for the reference user and an energization pattern.

In accordance with some illustrative embodiments disclosed herein, an FES system for generating an FES calibration database comprises: an FES device configured for connection with an associated body part of a user and including electrodes arranged to apply functional electrical stimulation to the associated body part of the user and further including sensors to measure a position of the associated body part; sensors configured to measure a set of body position measurements of the associated body part; and an electronic processor. The electronic processor is programmed to construct the FES calibration database by operations including receiving values of a set of user metrics for each reference user of a pool of reference users and further including, for each reference user of the pool of reference users and for each of a plurality of energization patterns: energizing the electrodes of the FES device in accordance with the energization pattern and measuring values for the set of body position measurements of a position assumed by the associated body part of the reference user in response to the energizing; and storing in the FES calibration database a record including fields containing the values of the set of user metrics for the reference user and the measured values of the set of body part position metrics for the position assumed by the associated body part of the reference user in response to the energizing.

In accordance with some illustrative embodiments disclosed herein, an FES system comprises an FES device configured for connection with an associated body part of a user and including electrodes arranged to apply functional electrical stimulation to the associated body part of the user and to perform EMG measurements of the associated body part of the user; and an electronic processor programmed to perform FES stimulation by operations including: acquiring EMG measurements of the associated body part of the user; determining a user-specific energization pattern based on the acquired EMG measurements of the associated body part of the user; and energizing the electrodes of the FES device in accordance with the determined user-specific energization pattern.

BRIEF DESCRIPTION OF THE DRAWINGS

FIG. 13 diagrammatically illustrates a muscle-to-electrode mapping suitably used for autocalibration based on a priori knowledge of muscle anatomy and detected EMG signals as described herein.

DETAILED DESCRIPTION

Figure 1:
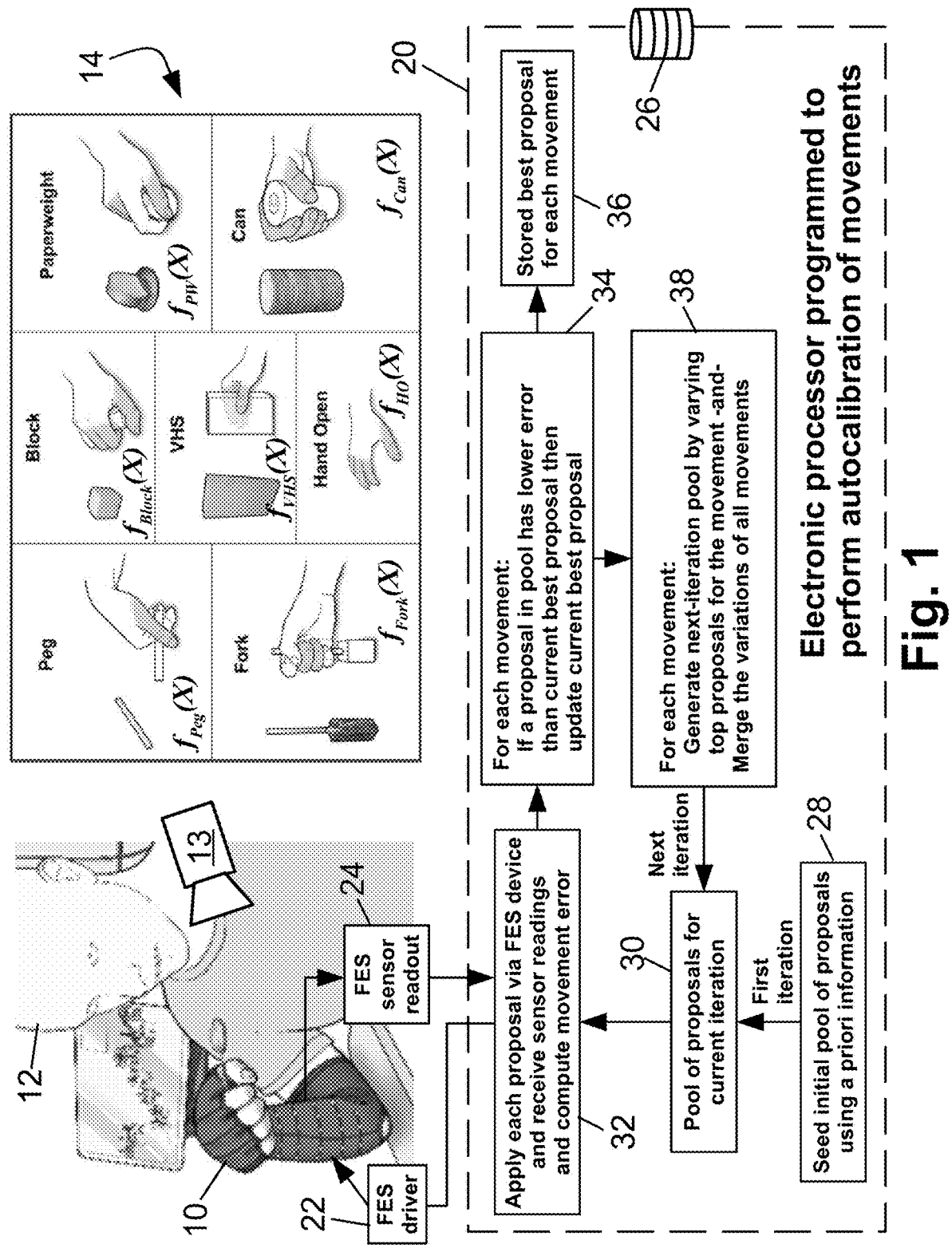
FIG. 1 diagrammatically illustrates an FES system including autocalibration components.

Various autocalibration systems are disclosed herein that reduce or eliminate the amount of labor-intensive FES system calibration performed by a physical therapist. The autocalibration optimizes an electrode energization pattern for producing each movement. In principle, various approaches can be used for optimizing such a problem, such as gradient-based optimization approaches, or metaheuristic optimization algorithms that operate by guided sampling of the solution space. Examples of metaheuristic algorithms include various genetic algorithms such as differential evolution (DE) and so forth. Gradient-based optimization is difficult to apply for FES system optimization, because the problem is not readily differentiable. On the other hand, metaheuristic optimizations operate by testing a population of candidate solutions, referred to herein as proposals, and do not require the problem to be differentiable. Hence, the approaches disclosed herein for autocalibration of an FES system employ a metaheuristic optimization.

In each iteration of a metaheuristic optimization, the proposals of a pool of proposals are measured using an error function. The proposals that are closest to producing the desired movement (as determined by the error function) are modified to generate the population pool for the next iteration. The illustrative examples employ DE for generating the population for the next iteration; however, other types of metaheuristic optimization algorithms such as various genetic algorithms may be employed. The iterative process is terminated when a proposal is identified that meets a predefined selection criterion, for example having an error (as measured by the error function) that is below a selection threshold.

Metaheuristic optimization approaches are well suited for problems in which the cost for scoring a proposal is low. In such cases, the population in each iteration can include many thousands, tens of thousands, or more proposals, and a satisfactory solution is usually efficiently achieved. However, for FES system calibration, the cost for scoring a proposal is high. A proposal in the FES system optimization task comprises an electrode energization pattern for the electrodes that specifies one or more energization parameters for each electrode, such as parameters indicating: whether the electrode is energized; applied voltage magnitude; applied voltage frequency; applied voltage waveform shape; various combinations thereof; or so forth. To score a proposal, the FES system must apply the proposal by actually applying the electrode energization pattern to the electrodes of the FES device, causing the muscles to contract in some way. This takes typically several seconds, and only one proposal can be tested at a time, and some resting time interval is usually provided before the next proposal is tested in order to allow the muscles to relax and to limit muscle fatigue.

Another problem recognized herein is as follows. The proposals are generated by a stochastic process in which the highest scoring proposals (that is, the proposals with lowest error metric as computed using an error function) of the last iteration are modified. Since the proposals are generated in an empirical fashion, there is a possibility that some proposals when applied during the scoring process may cause muscle contractions that are uncomfortable or even painful for the user. In this regard, it should be noted that a typical FES system for generating hand movements may apply voltages over 100 volts to muscles of the hand in order to induce muscle contractions.

Hence, the task of autocalibrating an FES system is very different from a more typical metaheuristic optimization task in which the proposals can be scored algorithmically, e.g. purely in software, with throughput of thousands, tens of thousands, or even more proposals being scored every second, with no concern about inducing discomfort or pain in a human user.

The FES calibration systems disclosed herein incorporate various improvements to address the foregoing problems and others.

In one improvement, seeding of the initial pool of proposals is done using a priori information. DE (and other metaheuristic algorithms) requires a set of initial parameters to start the optimization routine. A usual approach is to initialize with proposals comprising randomly generated sets of parameters. To accelerate the autocalibration procedure, and to reduce the likelihood of a randomly generated proposal inducing discomfort or pain, the disclosed FES system autocalibration optionally seeds the initial parameter set with values that are expected, based on a priori information, to be better than those generated purely at random. In one approach, proposals and target stimulation regions that have been successful in the past (as determined from manual calibration by an expert, previous autocalibrations, or parameters that have worked well on other users) may be employed for seeding the initial pool of proposals. By starting off closer to the target, the optimization is expected converge to a solution in less time as compared with random initialization. A combination of randomly generated and deliberately seeded parameters may optionally be used, so as to provide a good combination of informative starting values and random exploration.

Figure 3:
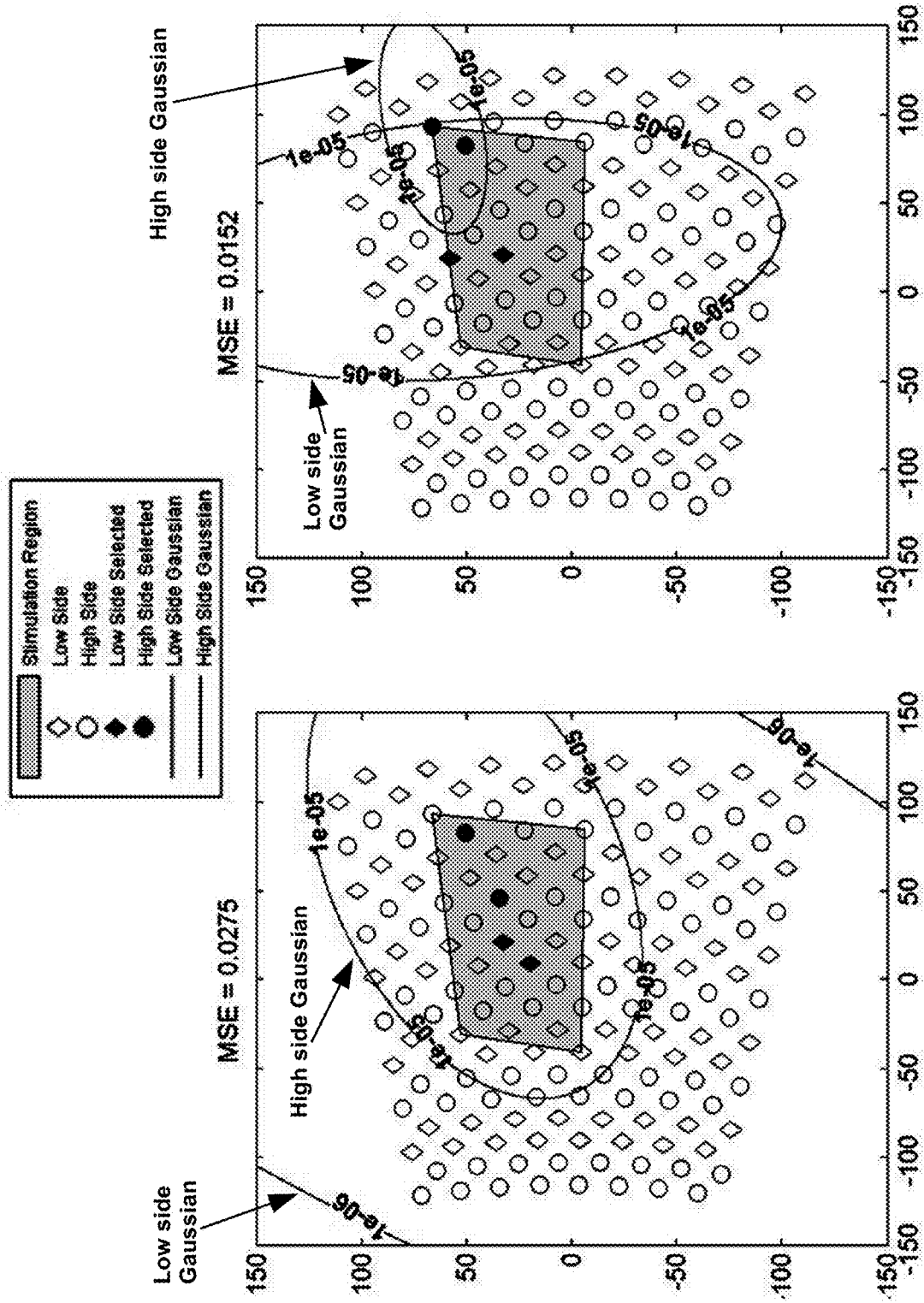
FIG. 3 diagrammatically illustrates an approach in which the stimulation pattern is represented within a grid of electrodes as two bivariate Gaussian distributions (high and low).

With brief reference to FIG. 3, in another improvement, the number of parameters is reduced. If parameters are assigned to each electrode individually that control whether the electrode is on or off, stimulation intensity, waveform or other features, then this leads to a large number of parameters to optimize making the problem difficult to solve efficiently. In this improvement, the stimulation pattern is represented within a grid of electrodes. FIG. 3 shows an illustrative approach in which the stimulation pattern is represented within a grid of electrodes as two bivariate Gaussian distributions (high and low) each with unknown means (two parameters) and unknown variance (three parameters). In addition, the amplitude of the stimulation pattern can be controlled by a parameter. Thus, the total number of parameters that need to be optimized in this illustrative example are at most 11 parameters. This represents a significant reduction in the number of parameters, although it does impose constraints on the types of patterns that can be generated. By reducing the number of parameters, the task solved by the optimization algorithm is simplified. This vector is then translated into a set of stimulation parameters, which are applied using the FES device and the resulting movement is measured by the sensors.

In another improvement, a weighted error function is used. As will be described, sensor readings from sensors of the FES device are received with the body part positioned by the applying of the proposal. The sensor information is used to determine how close the user's hand position is relative to the target, where "how close" is quantified by generating an error metric for the proposal with respect to the movement using an error function corresponding to the movement that depends on the sensor readings. In many cases the target movement is primarily characterized by certain sensors while others are relatively unimportant. For instance, in assessing the error metric for a wrist flexion movement, the sensor measuring the wrist position is highly relevant, whereas sensors measuring positioning of fingers are of less relevance. To account for this in the FES system autocalibration, a weighted mean square error (MSE) or other error function corresponding to the movement that comprises a weighted sum of squares where is used, with the squared error for each sensor is weighted by a predefined weight that can increase or decrease that sensors influence in the autocalibration.

In another improvement, in evaluating each proposal the amplitude of the electrode energization pattern applied to the electrodes of the FES device is ramped up, and the user is given a user input device (e.g. a button, squeeze ball, voice actuated stop, and/or the like) by which the user can stop the ramp if the user experiences discomfort or pain. The improvement is premised on the recognition herein that the autocalibration has the potential to generate stimulation patterns that may be uncomfortable or even painful to the user. To minimize discomfort, a ramping step is incorporated for the applying of each set of stimulation parameters defining a proposal. At the beginning of a session a maximum amplitude is set, and subsequently each proposed stimulation pattern is tested at low amplitude, and the amplitude is gradually increased to the maximum amplitude. At each step in the ramp, the user has the option to activate the user input device in order to stop the stimulation. Optionally, the user can further note via the user input device whether the stimulation was either starting to become uncomfortable or was considered painful. If the stimulation was becoming uncomfortable but not painful, then the stimulation is stopped for that proposal but the parameters and their associated scores prior to stopping are used in subsequent proposals. However, if the stimulation was becoming painful, then the parameter set is assigned a very large error metric ensuring that it will be avoided in future proposals, or the proposal is otherwise discarded.

In yet another improvement, multiple movements are optimized together. Most use cases of FES systems require the calibration of multiple movements. Typically, DE or other metaheuristic optimization algorithms optimize one problem at a time. Here, this would entail optimizing each movement separately, and repeating the DE optimization for each movement. It is recognized herein that this approach is inefficient. It is recognized herein that most of the time taken to score a proposal in the FES system optimization context is the time it takes to apply the proposal by energizing the electrodes of the FES device, with the second-longest time being to receive the sensor readings. These operations can be expected to take at least a second, and if ramping of the amplitude is employed then it may take up to 10 seconds or so to fully energize the proposal and read the sensors. On the other hand, computing the error metric using the error function applied to the sensor readings is very rapid, as this is entirely computer computations and can be done in a very small fraction of a second. Some FES system autocalibration embodiments disclosed herein leverage these insights to complete the autocalibration in less time and with less muscle stimulation to the user, by computing the error metric of each applied proposal with respect to each movement to be calibrated. The disclosed multiple-movement FES system autocalibration starts the same as a single-movement version, namely with a set of proposals to test (where the initial pool of proposals may be randomly generated, seeded, or a combination of these). Each proposal is actually applied using the FES device. However, in the multi-movement approach, the obtained position of the body part (as measured by the sensors of the FES device) are scored for all movements, by calculating the error metric for each movement using its corresponding error function applied to the sensor readings. Thereafter, new proposals for each movement are generated based on the set of all movements tested in the previous iteration. In this manner, each proposal provides information that is shared amongst all the movements and can be used to optimize each movement in one run of the metaheuristic optimization algorithm. To further improve the efficiency, in one approach the distances among a pool of new proposals for all movements are calculated, and a subset of proposals that fills the space the most is selected, i.e., if several similar proposals are generated for different movements, only one of them will be selected.

It should be noted that a given system or method of FES system autocalibration may employ any one of the foregoing improvements, or any two of the foregoing improvements, or so forth, or may employ all of the foregoing improvements. Furthermore, the improvement of ramping up the amplitude of the electrode energization pattern applied to the electrodes of the FES device may also be employed in manual calibration methods in which a physical therapist initiates the application of each proposal and assesses the error manually (e.g., without the use of sensors in the FES device, or alternatively with sensors in the FES device but evaluated manually).

With reference now to FIG. 1, an illustrative example of an FES system with autocalibration is described. The illustrative FES system is operative to stimulate hand movements, and to this end includes a function electrical stimulation (FES) device 10 configured for connection with an associated body part (here the hand and arm of a patient, subject, wearer, or other user 12). The FES device 10 includes electrodes arranged to apply functional electrical stimulation to the associated body part, and further includes sensors to measure a position of the associated body part. For the illustrative example, the sensors suitably measure the position of the wrist, hand, and fingers in real-time. More particularly, the illustrative FES device 10 includes a glove with bend sensors on each finger, and two additional inertial measurement unit (IMU) sensors to measure hand and/or wrist orientation. It will be appreciated that this is merely an illustrative example, and more generally the FES device may be designed to be arranged to apply FES to an associated body part such as a hand, wrist, arm, leg, foot, various combinations thereof, and so forth. Likewise, the sensors to measure a position of the associated body part are chosen based on the body part and the movements to be stimulated, e.g. for an FES device arranged to apply FES to a leg the sensors may include a bend sensor to measure bend at the knee and IMU sensors to measure orientation of the thigh and lower leg. More generally, the sensors to measure a position of the associated body part may include any combination of pressure sensors, strain gauges, accelerometers, micro-electro-mechanical system (MEMS) devices, 3-axis accelerometer, 3-axis magnetometer, a capacitive sensor including a flexible insulating dielectric layer sandwiched between flexible electrodes, a stretch sensor including a material that changes electrical resistance when stretched or strained, a resonant bend sensor including a resistance-inductance-capacitance (RLC) circuit, a sensor including at least one bladder configured to hold a fluid or air, a fiber optic cable and a measurement tool configured to measure a bend in the fiber optic cable based on a frequency or attenuation change in a signal of the fiber optic cable, a video motion tracking system (e.g. camera 13) configured to track a marker disposed on the associated body part, various combinations thereof, and/or so forth. By way of still further illustration, some further illustrative embodiments of some suitable FES devices are disclosed in Bouton et al., U.S. Pub. No. 2018/0154133 A1 published Jun. 7, 2018 and filed Jan. 16, 2018, titled "Neural Sleeve for Neuromuscular Stimulation, Sensing and Recording" which is incorporated herein by reference in its entirety.

The illustrative FES devices employ surface electrodes that contact the skin. In other embodiments, the FES device may employ implanted or transcutaneous electrodes that are implanted in or in contact with muscle tissue or pass through the skin to be in contact with muscle tissue. Moreover, while the illustrative FES devices employ a structural sleeve or glove to support the stimulation electrodes and sensors, it is also contemplated for the FES device to omit such structural support, in which case the FES device may, for example, include the electrodes arranged to apply FES to the associated body part and sensors to measure a position of the associated body part, without a sleeve, glove, or other structural element with which the electrodes and sensors are secured.

The illustrative FES system is to be autocalibrated to perform seven movements 14, as diagrammatically shown in FIG. 1 and summarized in Table 1. The seven movements include six grip movements (gripping a peg, a block, a paperweight, a fork, a VHS cassette tape, and a can) and a hand-open movement. Each movement 14 has an error function of the form $f\_(X)$ corresponding to the movement that depends on the sensor readings denoted by vector X. Again, these are merely illustrative examples, and for any particular application the choice of movements to be autocalibrated will depend on the associated body part and the tasks to be performed.

TABLE 1

Seven Movements to be Autocalibrated

| Movement | Error function |
| --- | --- |
| Grip a peg | $f_{Peg}(X)$ |
| Grip a block | $f_{Block}(X)$ |
| Grip a paperweight | $f_{PW}(X)$ |
| Grip a fork | $f_{Fork}(X)$ |
| Grip a VHS cassette tape | $f_{VHS}(X)$ |
| Grip a can | $f_{Can}(X)$ |
| Hand open | $f_{HO}(X)$ |

Each error function corresponding to a movement suitably comprises a weighted sum of squares (WSOS) where:

$$WSOS = \sum_{i=1}^{S} w_i(T_i - R_i)^2 \qquad (1)$$

where s=1, . . . , S indexes the sensor readings, $R_i$ is the $i^{th}$ sensor reading, $T_i$ is a target value of the $i^{th}$ sensor reading for the movement (so that $(T_i-R_i)^2$ is the square of the distance between the sensor position $R_i$ for the evoked movement and the target sensor position $T_i$ for the target movement), and $w_i$ is a weight assigned to the $i^{th}$ sensor reading for the movement. In some embodiments, the error function corresponding to the movement is the weighted sum of squares (WSOS). In some embodiments, the error function corresponding to the movement is a mean square error (MSE) given by $$\frac{1}{S}$$

(WSOS) where WSOS is the weighted sum of squares. In some embodiments, the error function corresponding to the movement is a root mean square error (RMSE) given by $$\sqrt{\frac{WSOS}{S}}.$$

These are merely illustrative examples. The error function quantifies the quality of the grips evoked by FES (or more generally, quantifies the quality of the movement evoked by applying the proposal).

The target sensor positions $T_i$, i=1, ..., S for a target movement can be determined in various ways. In one approach, an able-bodied person wears the FES device 10 and positions his or her hand at the target movement, and the sensor readings with the hand thusly positioned are the target sensor positions $T_i$, i=1, ..., S. In another approach, the target sensor positions $T_i$, i=1, ..., S can be determined using finite element modeling or the like.

With continuing reference to FIG. 1, an electronic processor 20 is programmed to perform autocalibration of the movements 14. By way of nonlimiting illustration, the electronic processor 20 may comprise a desktop computer, a notebook computer, a mobile device such as a cellphone or tablet computer, a dedicated electronic processor comprising a microprocessor, memory, and other associated electronics integrated on a circuit board (for example, a single-board computer such as a Raspberry PI), or so forth. The electronic processor 20 may in some embodiments comprise a microprocessor and associated electronics integrated into the FES device 10 itself. The electronic processor 20 is in operative communication with the FES device 10 to perform the calibration method. The operative connection may, for example, be by way of an FES driver 22 that receives digital waveforms representing voltages to be applied via the electrodes of the FES device 10 from the electronic processor 20 and includes digital-to-analog conversion (DAC) circuitry to convert the digital waveform to analog and electronic amplifiers to amplify the converted analog signals to the voltage amplitudes for the electrodes specified by the digital waveforms. The operative connection may further include an FES sensor readout component 24 that, for example, may include analog-to-digital conversion (ADC) circuitry to convert analog sensor signals output by the bend sensors and IMU sensors into digital form, combines the digitized sensor signals into a digital data packages (e.g. data packets, data vectors, or the like) and transmits the digital data packages to the electronic processor 20. These are merely examples. Moreover, it will be appreciated that the various electronic components 20, 22, 24 may be variously integrated or separate. For example, the sensor readout component 24 may be embodied as one or more ADC cards installed on a computer which embodies the electronic processor 20.

The electronic processor 20 is programmed to perform the disclosed autocalibration method by way of instructions stored on a non-transitory storage medium 26. The instructions stored on the non-transitory storage medium 26 are readable and executable by the electronic processor 20 to perform the calibration method to determine a calibrated electrode energization pattern (or patterns) for producing a movement (or movements) of the associated body part. The non-transitory storage medium 26 may, by way of nonlimiting illustration, comprise one or more of: a hard disk drive or other magnetic storage medium; a read-only memory (ROM), flash memory, or other electronic storage medium; an optical disk or other optical storage medium; various combinations thereof; and/or so forth.

With continuing reference to FIG. 1, the autocalibration employs an iterative calibration method. To initiate the first iteration, an operation 28 initially seeds a pool of proposals 30 for a current (initially first) iteration of the iterative calibration method. A default seeding is to initialize with proposals comprising randomly generated sets of parameters. However, to accelerate the auto-calibration procedure it is preferable to seed the initial pool of proposals with values (i.e., parameters defining various electrode energization patterns) based on a priori knowledge. For example, the seeding 28 may use parameter sets that have been successfully used with the specific user 12 in the past, for example obtained from manual calibration by an expert, or from previous auto-calibrations. Alternatively, the seeding 28 may use parameters that have worked well on other users. By starting off closer to the target by seeding based on a priori information, the optimization should converge to a solution in less time. A combination of randomly generated and deliberately seeded parameters may provide a good combination of informative starting values and random exploration.

The current pool of proposals 30 is generated by the seeding 28 for the first iteration, and for subsequent iterations is generated by the immediately preceding iteration as will be described. Each proposal of the pool 30 comprises an electrode energization pattern to the electrodes. As previously described with reference to FIG. 3, in some embodiments each electrode energization pattern is represented as follows. For a grid of electrodes (see FIG. 3) two bivariate Gaussian distributions (high and low) are defined, each with unknown means (2 parameters) and variance (3 parameters). In addition, the amplitude of the stimulation pattern can be controlled by a parameter. Thus, the total number of parameters that need to be optimized are at most 11. In some such embodiments, the number of parameters is further reduced as follows. First, the variance parameters of the two bivariate Gaussian distributions are set to constant values due to the fact that the variances typically do not strongly affect the selection of electrode location. Furthermore, if the amplitude is ramped up as discussed elsewhere herein, then the parameter that controls the amplitude of stimulation is eliminated as it is replaced by the ramping procedure. With those changes, the total number of parameters that need to be optimized are reduced to 6. It will be appreciated that this is merely an illustrative example, and more generally there are numerous ways that the electrode energization pattern can be parameterized to reduce the number of parameters so as to improve efficiency of the metaheuristic searching. The choice of parameterization suitably depends on number of electrodes, the arrangement of electrodes over the associated body part, the target movement(s), and so forth. More generally, the proposal comprising the electrode energization pattern is represented as at least one parameterized distribution over a group of electrodes, and the modifying of the proposals of the current pool of proposals (see operation 38, to be described later herein) comprises modifying values of the parameters of the at least one parameterized distribution.

At an operation 32, each proposal of the pool 30 is applied to the associated body part via the FES device 10. This entails computing the voltage waveforms for the electrodes, and sending the voltage waveforms to the FES driver 22 to cause it to drive the FES device 10 to apply the voltage waveforms to the associated body part via the electrodes of the FES device 10. That is, for each proposal of the current pool of proposals 30, the proposal comprising an electrode energization pattern is applied to the electrodes of the FES device 10, followed by receiving sensor readings from the sensors of the FES device 10 with the associated body part positioned by the applying of the proposal (e.g., via the FES sensor readout 24). An error metric is then generated for the proposal with respect to a movement (or, in some embodiments, with respect to several movements, e.g. with respect to each of the illustrative 7 movements 14) using an error function corresponding to the movement that depends on the sensor readings. For the illustrative 7 movements 14, this may entail applying each of the respective error functions:

$f_{Peg}(X)$, $f_{Block}(X)$, $f_{PW}(X)$, $f_{Fork}(X)$, $f_{VHS}(X)$, $f_{Can}(X)$, and $f_{HO}(X)$, to the sensor readings (represented by the vector X in this example), so as to generate error metrics for the corresponding movements: Grip a peg; Grip a block; Grip a paperweight; Grip a fork; Grip a VHS cassette tape; Grip a can; and Hand open. (See Table 1). As previously discussed, the error functions may, for example, be WSOS, MSE, RMSE, or other error functions. In this multi-movement calibration embodiment, a movement-specific sum-of-squares $WSOS_{Movement}$ for a particular movement can be written as follows:

$$WSOS_{Movement} = \sum_{i=1}^{S} w_{i,Movement}(T_{i,Movement} - R_i)^2 \quad (2)$$

where s=1, ..., S indexes the sensor readings, $R_i$ is the $i^{th}$ sensor reading, $T_{i,Movement}$ is a movement-specific target value of the $i^{th}$ sensor reading for the movement, and $w_{i,Movement}$ is a movement-specific weight assigned to the $i^{th}$ sensor reading for the movement. To allow for the movement-specific sum-of-squares $WSOS_{Movement}$ to be comparable across the multiple movements, it may be beneficial to normalize the weights for each movement, e.g. by applying the following normalization constraint:

$$\sum_{i=1}^{S} w_{i,Movement} = 1 \quad (3)$$

With continuing reference to FIG. 1, at an operation 34, for each movement it is determined whether any proposal in the current pool 30 has lower error metric than the current best proposal for that movement stored in a temporary storage 36. If so, then the temporary storage 36 is updated with the proposal of the current pool 30 having the lowest error metric for that movement. (For the first iteration, the temporary storage 36 is empty, so it is updated with the best proposal of the first-iteration pool for each movement.)

In an operation 38, an updated pool of proposals for a next iteration of the iterative calibration method is generated by modifying the proposals of the current pool 30 based on the generated error metrics. This updated pool of proposals then becomes the current pool 30 for the next iteration. The updating of the pool may be done using the Differential Evolution (DE) algorithm or another genetic algorithm, or more generally some other metaheuristic updating algorithm.

In a preferred embodiment for use when multiple movements are to be calibrated (e.g., the seven movements 14 detailed in Table 1), the approach for the operation 38 of updating the pool is as follows. For each movement of the plurality of movements 14, a movement-specific pool of proposals is generated by modifying the proposals of the current pool 30 based on the generated error metrics for the movement. Then, the movement-specific pools of proposals for the plurality of movements are combined to generate the updated pool of proposals for the next iteration. The combining of the movement-specific pools to generate the next iteration pool for use as the current pool 30 in the next iteration can employ various approaches. In one approach, if the pool 30 is to have P=70 proposals and there are M=7 movements 14 being calibrated, then each movement-specific pool of proposals can be generated with 10 proposals, and the combined pool then includes the 10 proposals for each of the 7 movements. (More generally, in this approach each movement-specific pool would have P/M proposals).

In another approach for combining the movement-specific pools, the contribution of each movement-specific pool to the final pool for the next iteration is set based on how close the current best proposal in the storage 36 for that movement is to the ideal movement. For example, if the $WSOS_{Movement}$ expression of Equation (2) is used with the weights normalization constraint of Equation (3), then in general the smaller the value of $WSOS_{Movement}$ is for the current best proposal for a given movement, the closer that best proposal is to the ideal movement. In this case, if the pool is to have P proposals and there are M movements, then the contribution of proposals for a given movement to the final pool 30 may be proportional to or functionally dependent on P/M scaled by the value of $WSOS_{Movement}$ is for the current best proposal for that movement. More generally, movements whose current best proposal is close to the ideal movement contribute fewer proposals to the next iteration pool 30; whereas, movements whose current best proposal is far away from the ideal movement contribute more proposals to the next iteration pool 30. This ensures that the pool 30 does not overemphasize variants of already-close best proposals. In some such embodiments, if the current best proposal for a certain movement has an error metric that meets a stopping criterion indicating the best proposal is close enough to be used in performing practical tasks (e.g., its error metric is below a stopping threshold value), then no further movement-specific pools are computed for that movement (as it is already "solved" as defined by the stopping criterion).

The iterative calibration method implemented by the processing loop 30, 32, 34, 38 selects, based on the error metrics, the calibrated electrode energization pattern for producing a movement from the proposals applied during one or more iterations of the iterative calibration method. To this end, there is typically some stopping criterion defined. For example, the process may stop for a given movement when the operation 34 stores a proposal in the temporary storage 36 for that movement whose error metric is below a predefined termination threshold value. For a multi-movement autocalibration, the stopping may occur when such a stopping criterion is satisfied for every movement being calibrated.

Figure 2:
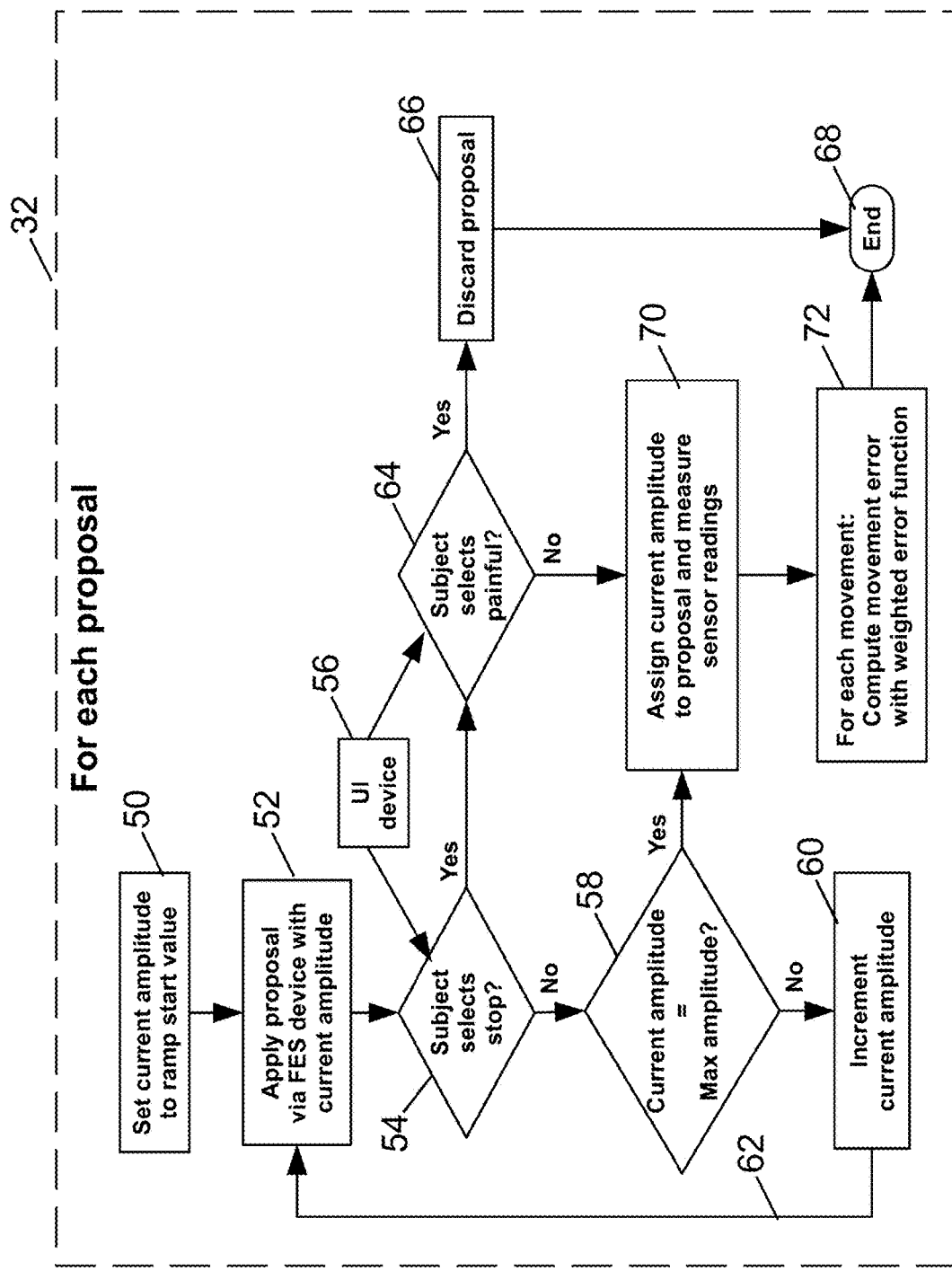
FIG. 2 diagrammatically illustrates a suitable approach implemented in the context of the FES system of FIG. 1 for applying each proposal via the FES device and scoring the proposal.

With reference now to FIG. 2, an illustrative embodiment of a suitable implementation of the operation 32 is described, which implements the ramping of the stimulation amplitude. The processing loop shown in FIG. 2 is performed for each proposal in the pool 30. A maximum amplitude is predefined, for example this may be a configurable setting of the autocalibration. At an operation 50, a current amplitude for applying the proposal is set to a ramp start value, which is a low value (for example, 5% of the maximum amplitude). At an operation 52, the proposal is applied via the FES device 10 at the current amplitude. At an operation 54, it is determined whether the user 12 has activated a user input (UI) device 56 that is given to the user to indicate if a proposal is causing discomfort or pain. The UI device 56 is a device that the user 12 can quickly and easily operate to indicate a sensation of discomfort or pain. The choice of physical embodiment of the UI device 56 depends on factors such as cost and the physical ability of the user 12. For example, if the user 12 has a paralyzed right hand (as shown in FIG. 1), but his or her left hand is fully functional, then the UI device 56 can be a hand-operated button, squeeze ball, or the like which the user 12 operates using his or her left hand. On the other hand, if the user 12 is a tetraplegic who has all four limbs paralyzed but retains use of his or her voice, then the UI device 56 may be a microphone that detects a predefined vocal signal indicating discomfort or pain. If the user 12 is a tetraplegic who has all four limbs paralyzed and also is unable to vocalize, but can move his or her eye gaze, then the UI device 56 may be an eye movement or gaze detector that detects a predefined eye movement signal indicating discomfort or pain. For example, the user 12 may be instructed to gaze upward to indicate discomfort or pain. In embodiments in which the FES system is driven by a brain-computer interface (BCI), then it is contemplated that the UI device 56 may be the BCI which detects when the user 12 is experiencing discomfort or pain. (To be suitable, the BCI would need to detect this with a high degree of accuracy).

With continuing reference to FIG. 2, if the user 12 does not select to stop at the decision block 54, then flow passes to a decision block 58 that checks whether the current amplitude is the predefined maximum amplitude. If not, then the current amplitude is incremented at an operation 60 and flow passes back to operation 52 as indicated by return arrow 62 in order to apply the next step of the amplitude ramp. Hence, it is seen that the process flow 50, 52, 54, 58, 60, 62 operates to ramp up the amplitude of the electrode energization pattern applied to the electrodes of the FES device 10, with the ramping stopping in response to the first to occur of (i) the amplitude reaching a maximum amplitude (via decision 58) or (ii) receiving a user-generated stop signal (via decision 54, where the user-generated stop signal is generated by activation of the UI device 56 by the user 12).

In the illustrative example of FIG. 2, in the case in which the user 12 selects to stop at decision 54, flow passes to a further decision where the user 12 is to indicate whether he or she selected stop at decision 54 due to discomfort or pain. This selection can be done in various ways, depending upon the nature of the UI device 56. For example, if a squeeze ball is the UI device 56, then the user 12 may squeeze once to indicate discomfort, or twice in rapid succession to indicate pain. In the case of a microphone or gaze detector serving as the UI device 56, the user 12 can supply a predetermined response to indicate discomfort or another predetermined response to indicate pain (e.g., for a microphone, voice recognition can be used to detect a keyword such as "pain"; or for a gaze detector directing the gaze down can be predefined as indicating "pain"). If the user indicates at decision 64 that the stimulation was painful, then at an operation 66 the proposal is discarded. This can be implemented in various ways, such as removing the proposal from the pool 30 or by assigning a very high error metric for the proposal thereby ensuring it will not be further considered. Flow then passes to the end block 68 indicating that the operation 32 has completed processing for the proposal being scored.

On the other hand, if the ramping process flow 50, 52, 54, 58, 60, 62 stops because the maximum amplitude has been reached (per decision block 58) or because the user 12 selects stop at decision 54 but indicates the proposal was merely causing discomfort (but not pain) at decision 64, then process flow passes to an operation 70 where the current amplitude is assigned to the proposal (this will be either the maximum amplitude if the ramp was stopped at decision 58, or the amplitude at which the user 12 selected stop at decision 54), and the sensor readings are measured (e.g., via the FES sensor readout 24 of FIG. 1). At an operation 72, the error metric for the proposal is computed for each movement being calibrated. This may be done, for example, using the WSOS of Equation (1) if only a single movement is being calibrated; or using the $WSOS_{Movement}$ of Equation (2) for each movement if multi-movement calibration is being done. The operation 72 may alternatively use a different error function formulation, e.g. a weighted MSE or weighted RMSE. Process flow then passes to the end block 68 indicating that the operation 32 has completed processing for the proposal being scored.

The output of the autocalibration is a calibrated electrode energization pattern for producing each movement of the set of movements 14. Thereafter, the user 12 can use the FES system to produce these movements. To do so, the electronic processor 20 receives or generates a command signal to perform a specific movement, and in response to the received or generated command signal, the calibrated electrode energization pattern for producing the specific movement is applied to the electrodes of the FES device 10 to produce the movement of the associated body part. The electronic processor 20 may receive the command signal in various ways, such as by the user 12 operating a computer embodying the electronic processor 20 to supply the received command signal. An example of this is the user 12 looking at an icon displayed on a display of the computer wherein a gaze detector, not shown, detects that the user 12 is looking at the icon. In another embodiment, the user 12 has a brain-computer interface (BCI) for producing the command signal. In some such embodiments, the electronic processor 20 also implements a brain neural activity decoder to analyze brain neural activity of the user 12 so as to generate the command signal. Alternatively, the processor of the BCI may be separate from the electronic processor 20 that performs the autocalibration and controls the FES device 10, in which case the electronic processor 20 receives the command signal from the separately implemented BCI. These are merely nonlimiting illustrative examples of ways that the user 12 can produce the command signal that is received or generated by the electronic processor 20.

Referring back to FIG. 2, it is further noted that the approach of ramping up the amplitude of a proposal can be useful even in a manual calibration context. For example, in a manual context a physical therapist may select a candidate electrode energization pattern based on the experience of the physical therapist. The physical therapist then applies the candidate electrode energization pattern to the electrodes of the FES device. If this is done without ramping as is conventional, then if the physical therapist made a poor choice of candidate electrode energization pattern it could cause discomfort or even pain to the user 12. However, by ramping up the amplitude of the electrode energization pattern applied to the electrodes of the FES device 10 and stopping the ramping in response to the first to occur of (i) the amplitude reaching a maximum amplitude or (ii) receiving a user-generated stop signal, as per the process flow 50, 52, 54, 58, 60, 62 of FIG. 2, the user 12 is protected from the physical therapist making a poor choice of candidate electrode energization pattern.

Figure 4:
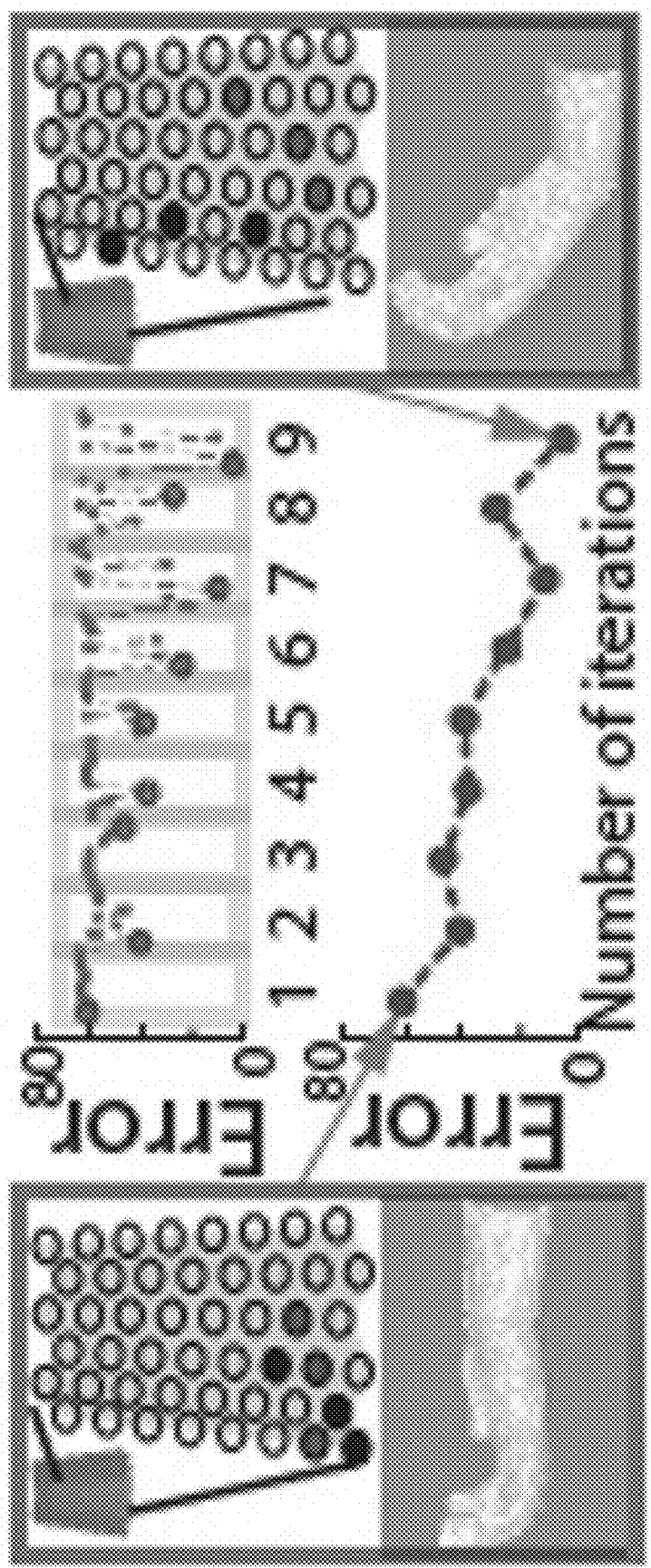
FIG. 4 diagrammatically illustrates an autocalibration experiment result, in which the experiment started at a set of randomly selected electrode patterns (iteration 1), and then the autocalibration algorithm automatically identified and tested patterns that gradually reduced the error rates until the error rate is below the predetermined threshold.

In the illustrative example of FIG. 4, the autocalibration algorithm was used to calibrate electrode energization pattern for wrist flexion, in which the number of proposals in each iteration and the threshold of the error rate were set up as 8 and 5%, respectively. A set of proposals were randomly generated in the first iteration, all of which produced relatively high error rates. Then, the autocalibration algorithm generated proposals for each iteration guided by the optimal result from previous iteration, and the error rates gradually decrease over the iterations. The experiment was stopped after $9^{th}$ iterations because the error rate was below the 5% threshold.

In the following, some additional autocalibration approaches are described. These may be used alone, or in combination with the autocalibration approach of FIGS. 1-4, for example to provide a basis for the initial pool of proposals 28 seeded on the basis of a priori information. The additional autocalibration approaches are suitably implemented in conjunction with the FES system of FIG. 1 including the FES device 10, FES driver 22 and the electronic processor 20 and non-transitory storage medium 26, and in some embodiments also including the FES sensor readout 24 and/or camera 13. The additional embodiments entail different autocalibration methods implemented by the electronic processor 20 and non-transitory storage medium 26.

Figure 5:
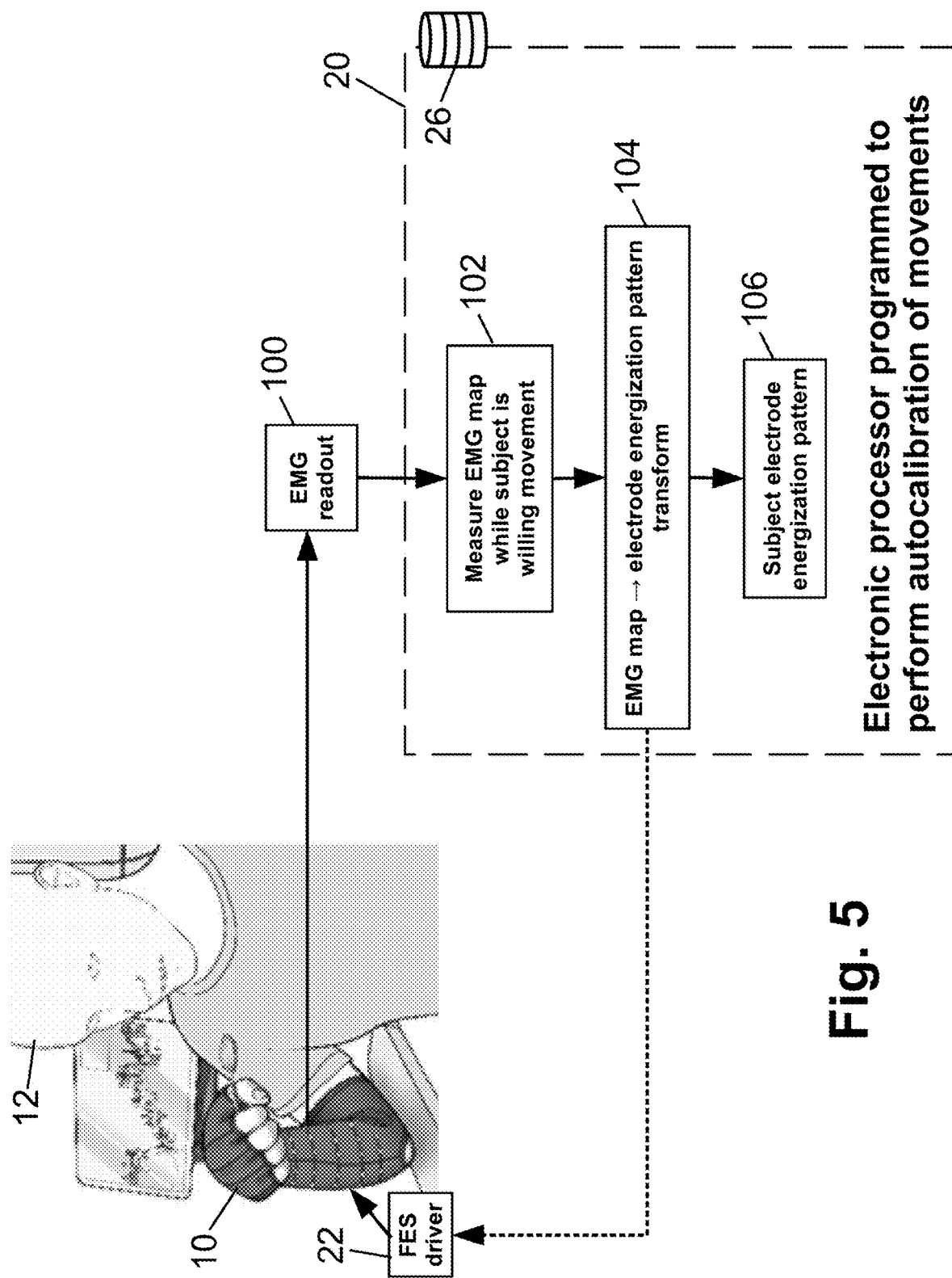
FIGS. 5, 6, and 7 diagrammatically illustrate autocalibration embodiments that utilize EMG mapping.

With reference to FIG. 5, an approach is described which relies upon an electromyography (EMG) signals readout 100 detecting electromyography (EMG) signals generated by the muscles themselves in response to the user 12 willing the intended movement. As previously noted, the FES device 10 may (and in this embodiment does) also includes electrodes (which may be the same as the stimulation electrodes or a different set of electrodes) that detect EMG signals generated by the muscles themselves in response to the patient 12 willing the intended movement. It is assumed that the EMG signals are not sufficient by themselves to cause the intended movement, for example due to a spinal cord injury (SCI) attenuating the communication from the brain or due to limitations on autonomous movement control due to a stroke). In this regard, it is noted that some studies have found that EMG signals are detectable even in the case of a SCI that is clinically determined to be a "complete" SCI. This autocalibration approach also assumes that the EMG signals detected by the EMG readout 100 are at least reasonably close to those that would be produced in the absence of the clinical disability (e.g. SCI or stroke). By contrast, in some stroke patients for example, this criterion may not be met as the effects of the stroke may cause the motor neural signals from the brain to be misdirected.

With continuing reference to FIG. 5, the electronic processor 20 is programmed (e.g. by software, firmware, or other instructions stored on the non-transitory storage medium 26) to perform operations as here described. In an operation 102, the EMG readout is used to measure an EMG map while the user 12 is willing the intended movement. The EMG map is a surface plot of EMG signals over the surface covered by the electrodes of the FES device 10. It is noted that the FES driver 22 is not operating to apply any energization pattern during the EMG readout operation 102. (Even if two separate sets of electrodes are used for FES and EMG respectively, the applied FES signals are typically much stronger than the EMG signals and might hinder or prevent accurate measurement of the EMG map). In an operation 104, the EMG map is transformed to generate the user electrode energization pattern 106. This transform 104 generally includes at least a scaling transform to convert the low amplitude EMG signals to substantially higher amplitude FES energization levels. The scaling can, for example, be a linear scaling set to transform the highest-magnitude EMG signal to a pre-defined target maximum FES energization level. In a variant approach, the operation 104 can determine the transform by operating the FES driver 22 to apply an electrode energization pattern matching the EMG map in shape, and ramping up the amplitude of the electrode energization pattern applied to the electrodes of the FES device until the intended movement is obtained or until the patient indicates discomfort or pain. This ramping can, for example, be applied in accordance with operations 50, 52, 54, 58, 60 of FIG. 2, already described. If the intended movement is obtained then the ramp value at which the intended movement is obtained is the amplitude set for the user electrode energization pattern 106. In effect, the approach of FIG. 5 operates as an amplifier (possibly non-linear) which amplifies the insufficient EMG signals generated by the user 12 in order to actually perform the volitionally intended movement.

Advantageously, the embodiment of FIG. 5 does not require the FES sensor readout 24 for measuring hand position. However, the autocalibration approach of FIG. 5 may be ineffective if certain conditions are not met. The approach of FIG. 5 assumes that the user 12 is able to generate the EMG signals at a level sufficient to be accurately measured at the operation 102 by willing the intended movement. This may not be the case in a SCI patient. The approach of FIG. 5 further assumes that the patient's nervous system accurately transfers the volitional intent generated in the brain to the motor nerves in the arm. This may not be the case in a stroke victim. On the other hand, the approach of FIG. 5 is straightforward to implement, and in many cases is expected to produce at least a relatively accurate user electrode energization pattern 106. Optionally, this user electrode energization pattern 106 may serve as a starting point for manual fine-tuning of the electrode energization pattern, or may serve as a priori information for seeding the initial pool of proposals 28 (see FIG. 1) if the autocalibration approach of FIG. 1 is then subsequently employed.

Figure 6:
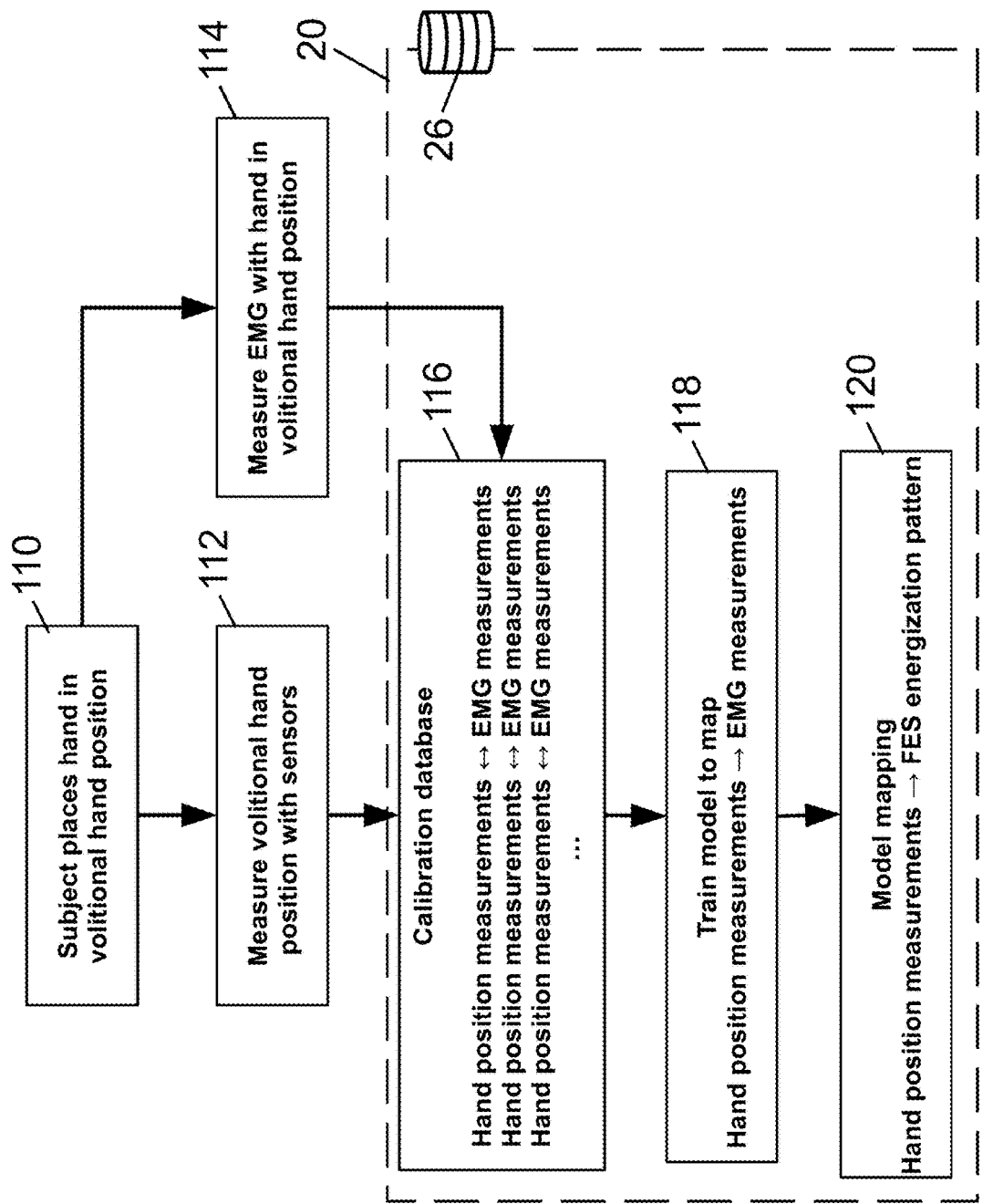
Figure 7:
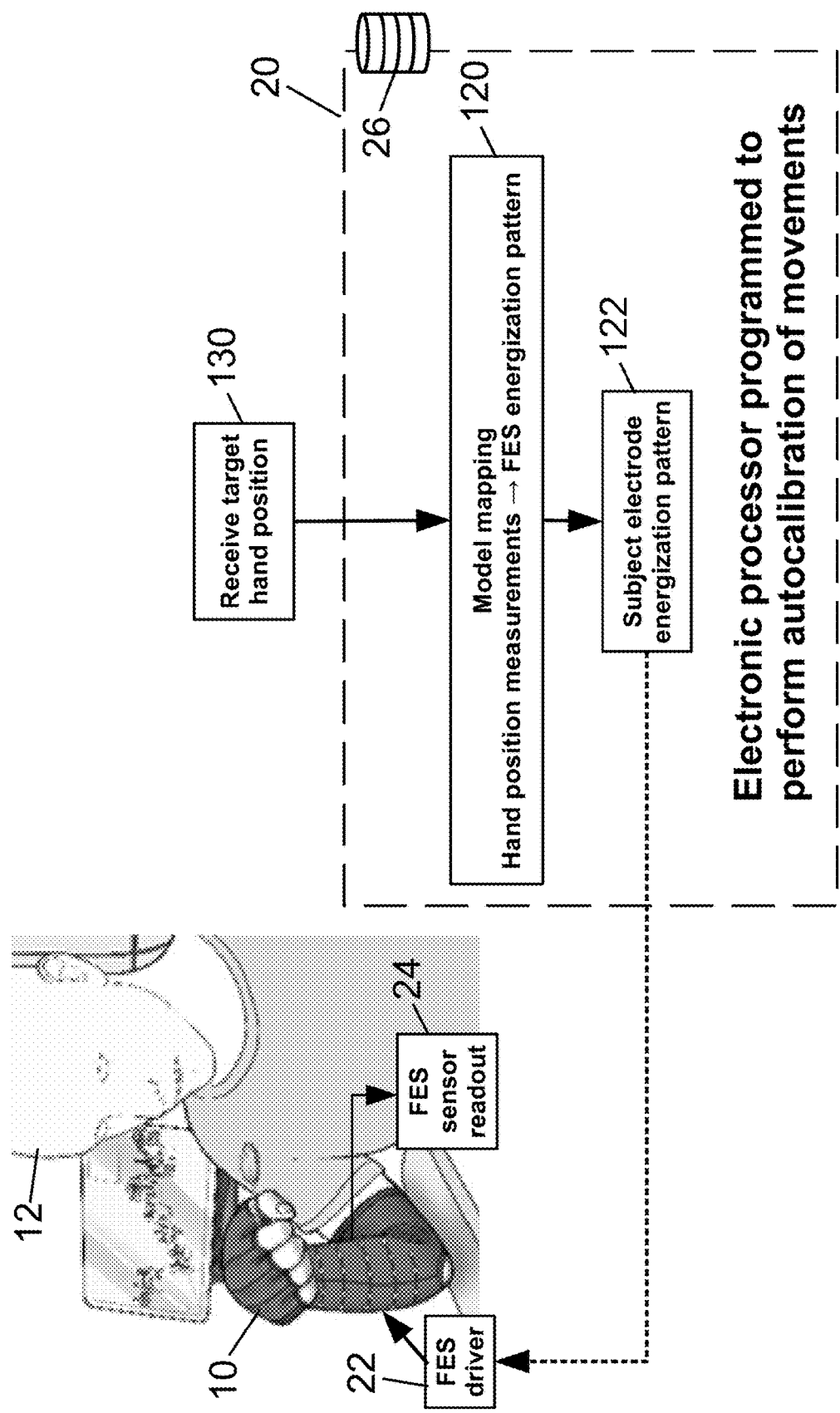

With reference now to FIGS. 6 and 7, an approach is described that is suitably used for an able-bodied user, and possibly also for a user with SCI if some residual EMG is detectable in the arm muscles. This approach employs a model training phase (FIG. 6) and a model application phase (FIG. 7), where again the electronic processor 20 is programmed (e.g. by software, firmware, or other instructions stored on the non-transitory storage medium 26) to perform the described operations (other than operations identified herein as manual operations). Typically, both the model training (FIG. 6) and the model application (FIG. 7) are performed by the same user. In the training phase of FIG. 6, in an operation 110 the user places his or her hand in a volitional hand position, and this position is measured by sensors in an operation 112 (e.g. using the FES sensor readout 24 such as bend sensors to measure finger joint angles and one or more IMU sensors to measure hand and/or wrist orientation, and/or so forth; and/or using the camera 13, see FIG. 1). More particularly, at the operation 112 values are measured for a set of hand position measurements with the hand placed in the volitional hand position. The set of hand position measurements may include the readings of the bend sensors, IMU sensors, and/or other positional sensors. Alternatively, if the camera 13 is used then the set of hand position measurements may include finger joint angles, hand and/or wrist orientation, et cetera extracted from frames of the video acquired by the camera 13. Additionally, with the hand in the volitional hand position produced in operation 110, EMG measurements are made in an operation 114. If the user is able-bodied, then the operation 110 may be manually performed by the able-bodied user volitionally placing the hand into the intended position. In the case of an SCI patient, the operation 110 may be performed by a human assistant (e.g. physical therapist) placing the hand into the intended position while the SCI patient volitionally wills the hand to assume that position.

In a variant approach, the measurement 112 of the hand position may be omitted. In this variant approach, the operation 110 in which the user 12 places the hand in the volitional hand position is performed at given times in response to cues generated by the electronic processor 20 (e.g. by displaying a graphical model of the intended hand position on a display), and the hand is assumed to be in the volitional hand position at a fixed time after the cue. The EMG measurement 114 is performed at that fixed time after the cue. In this approach, the hand measurement operation 112, and the corresponding hand position sensors, are optionally omitted, and the calibration database 116 stores the intended volitional hand position rather than actually measured hand position measurements.

The operations 110, 112, 114 are repeated for a range of hand positions so as to construct a calibration database 116 that stores (Hand position measurements, EMG measurements) pairs. In an operation 118 this database 116 is used to train a model to map values of the set of hand position measurements to EMG measurements. Any suitable machine learning (ML) component may be employed for the operation 118, such as an artificial neural network (ANN) that receives as input the values of the set of hand position measurements and outputs the EMG measurements on the electrodes of the FES device 10. Backpropagation training can be used to optimize learned parameters of the ANN (e.g., weights and activation function parameters of the ANN) to output the EMG measurements in response to the corresponding values of the set of hand position measurements for the pairs stored in the database 116. Instead of an ANN, the ML model may be a support vector machine (SVM), regression model, Bayesian network, or so forth.

The resulting model mapping hand position to EMG measurements is then converted to a model 120 mapping values for the set of hand position measurements to FES energization pattern. To do this, the transformation used in the operation 104 (see FIG. 5) in which the EMG map is transformed to generate the user electrode energization pattern may be employed. Again, this transform generally includes at least a scaling the low amplitude EMG measurements to substantially higher amplitude FES energization levels.

Turning now to FIG. 7, in the model application phase, a target hand position is received in an operation 130. For example, in a gaming, VR, or AR system, the target hand position may be received from that system. In the case of therapy for an SCI patient, the target hand position may be received from a brain-computer interface (BCI). These are merely illustrative examples. The target hand position is received in the operation 130 as values for the same set of hand position measurements as were acquired in the operation 112 of the training phase (FIG. 6). Hence, the model 120 mapping hand position measurements to FES energization pattern which was generated in the training phase (FIG. 6) may be directly applied, so as to generate a user electrode energization pattern 122 for energizing the FES device 10 to produce the target hand position received at the operation 130.

The approaches of FIGS. 5-7 operate on an expected correlation between EMG measurements acquired when the user is volitionally intending a movement and the FES energization pattern for producing that movement. This expectation may not hold in some situations, such as stroke patients whose EMG signals may be mixed up, or SCI patients who may be unable to volitionally generate detectable EMG signals.

Figure 8:
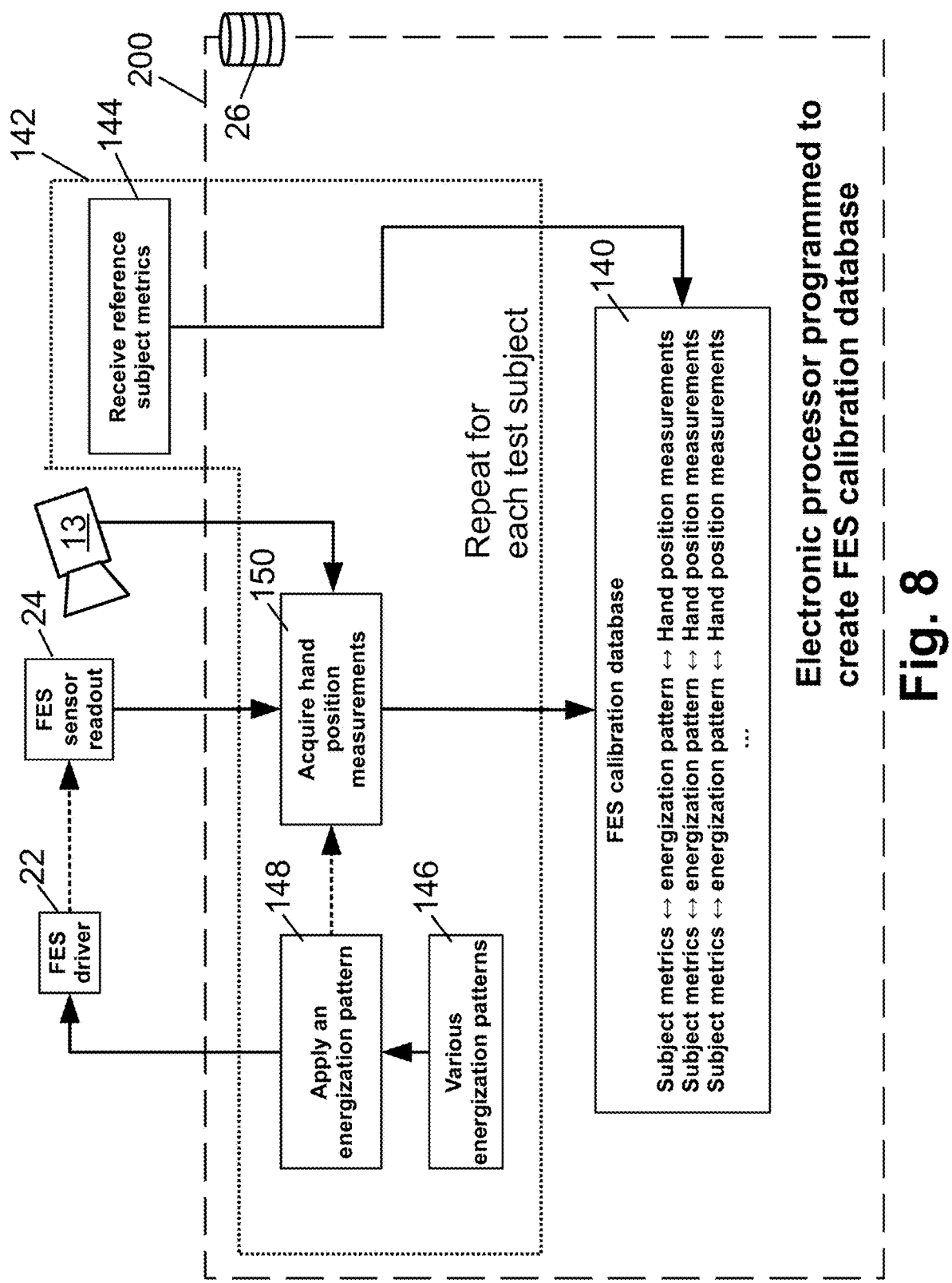
FIGS. 8, 9, and 10 diagrammatically illustrate autocalibration embodiments that utilize a database of FES calibration data collected for a pool of reference users.
Figure 9:
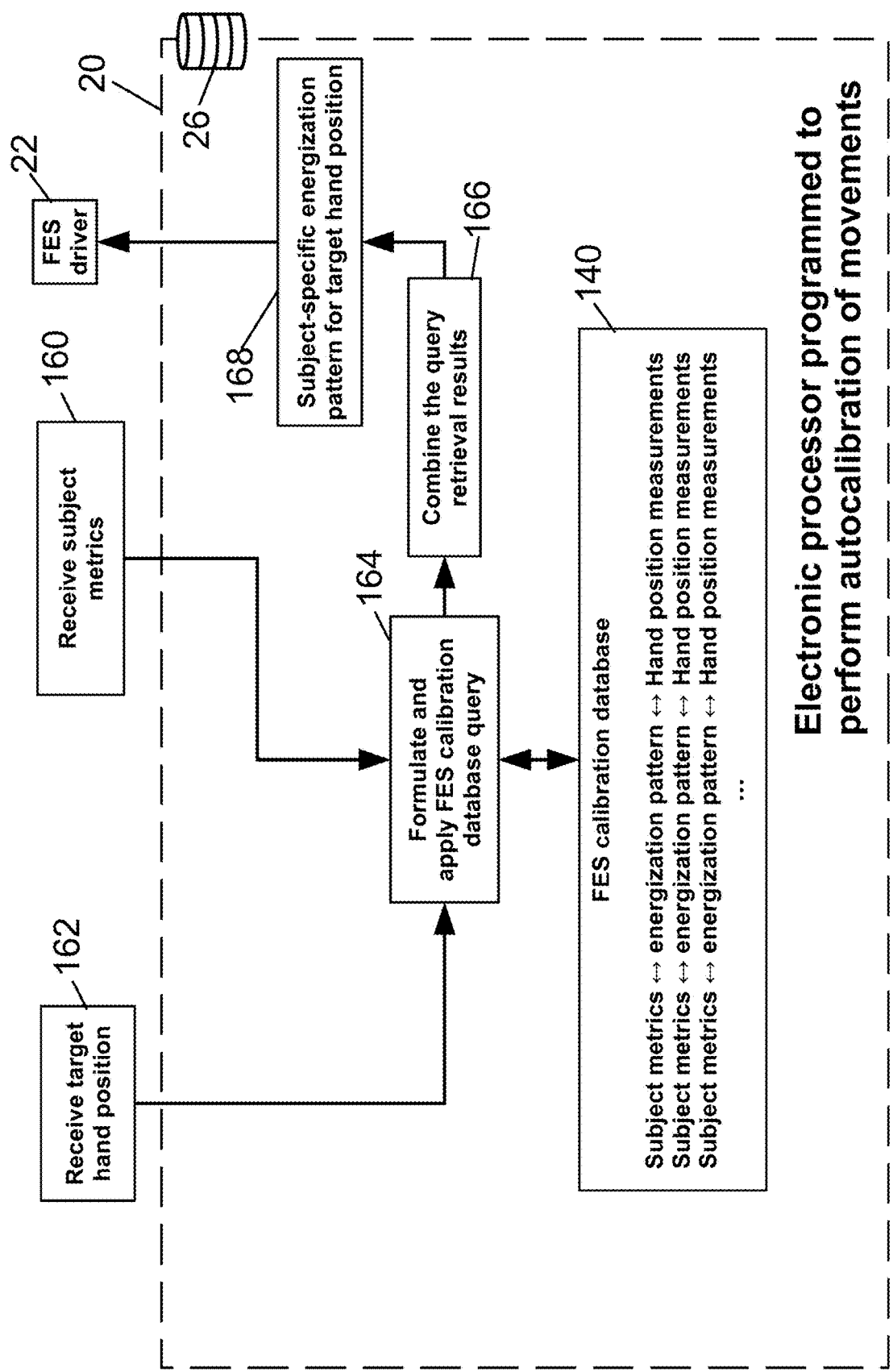

With reference to FIGS. 8 and 9, an approach is described that is suitably used in situations in which the EMG cannot be measured or cannot be reliably mapped to an energization pattern, or more generally for any calibration of the FES device 10. The approach of FIGS. 8 and 9 entails constructing an FES calibration database 140 (FIG. 8) and then querying the FES calibration database 140 (or alternatively, using a model trained using the contents of the FES calibration database 140) to generate the FES energization pattern for a particular movement. Again, the electronic processor 20 is programmed (e.g. by software, firmware, or other instructions stored on the non-transitory storage medium 26) to perform the described operations (other than operations identified herein as manual operations).

Starting with FIG. 8, the construction of the FES calibration database 140 is described. This is done using a pool of reference users, who may be all able-bodied, or may all be impaired users (e.g. impaired by a stroke or SCI), or may be some combination of able bodied and impaired users. A process 142 is performed in conjunction with each reference user to generate database content for that reference user. At an operation 144, values for a set of user metrics are received. For example, the set of user metrics may include dimensional measurements of the body part (here arm) to which the FES is to be applied, such as (for the illustrative arm) forearm length, wrist circumference, one or more additional standardized arm circumference measurements (e.g., at ¼, ½, and ¾ of the distance from the wrist to the elbow), and/or so forth. It is further contemplated for the set of user metrics whose values are received at the operation 144 to include other anatomical information besides dimensional measurements, such as: positional measurements of relevant anatomical parts, such as positions of major blood vessels or specific muscles in the arm (see, e.g. FIG. 13 and related text); demographic metrics such as birth gender and/or ethnicity; height, weight, body mass index (BMI), or other overall anatomical metrics; arm strength and/or arm muscle tone metrics (or, more generally, strength and/or tone metrics for specific muscles/muscle groups); and/or so forth. The set of user metrics is preferably limited to user metrics that may credibly be expected to impact the energization pattern for producing a specific movement of the target anatomy, and it will be appreciated that the specific set of user metrics may depend on factors such as the body part being energized by the FES device 10, the types of target movements, and so forth. The user then dons the FES device 10, and various energization patterns 146 are applied. The various energization patterns 146 preferably span a representative range of the hand positions and movements that it is desired to calibrate. However, the various energization patterns 146 do not need to be precisely pre-calibrated to produce specific hand positions in the reference user. Indeed, in some contemplated embodiments, the various energization patterns 146 may be randomly generated, or may be a set of pre-defined energization patterns that do not necessarily correlate with any specific hand position. Alternatively, the various energization patterns 146 may be (at least coarsely) designed to produce specific hand positions. Various combinations of pre-defined and randomly generated energization patterns are also contemplated.

More specifically, in the user process 142, for each energization pattern of the various energization patterns 146, the energization pattern is applied in an operation 148 to the reference user's arm via the FES driver 22 of the FES device 10, and the hand position stimulated by the FES energization pattern application 148 is measured in an operation 150. More particularly, the operation 150 measures values for a set of hand position measurements. As already described with reference to operation 112 of FIG. 6, the set of hand position measurements may include sensor readings of bend sensors configured to measure finger joint angles, readings of one or more IMU sensors monitoring hand and/or wrist orientation, and/or so forth; or may include analogous measurements obtained by analysis of video frames acquired by the camera 13.

In this way, for each user processed by process loop 142 and for each of the various energization patterns 146, a database record including three fields is generated as follows:

(user metrics field, energization pattern field, hand position measurements field)

where: the user metrics field contains the user metrics for the reference user obtained at the operation 144; the energization pattern field contains the energization pattern applied at the operation 148 (for example, as voltages or currents applied to various electrodes or groups of electrodes of the FES device 10); and the hand position measurements field contains the values for the set of hand position measurements acquired at the operation 150. It is noted that the order of the fields may be different that that mentioned above, and moreover the logical structure of the records may be different (e.g., the user metrics field may be broken into two or more different fields, such as a dimensional metrics field, a muscle strength field, et cetera). It will be appreciated that any single reference user may provide a large number of records for inclusion in the database 140, with each record having the same user metrics field content, but different energization pattern fields and different hand position measurements fields. For example, if the various energization patterns 146 include 200 different patterns, then a single reference user contributes 200 records to the FES calibration database 140. If there are 100 reference users, then this allows for relatively rapid addition of 20,000 records in the database.

In one non-limiting contemplated specific approach for performing the database construction of FIG. 8, each reference user is expected to perform the process 142 over a 2-3-hour session. Each session 142 will involve measuring the user's arm (operation 144), donning the sleeve (specific example of FES device 10), and manually calibrating six patterns for functional hand/wrist movements, including: Hand Open, Hand Close, Wrist Extension, Wrist Flexion, Ring Flexion, and Lateral Pinch. Additional or alternative movements are contemplated (e.g., see Table 1). The stimulation patterns will be manually calibrated using a graphical user interface (GUI) that allows for rapid stimulation pattern variational changes (e.g. button to shift active electrode groups, button to flip polarity, button to randomly scatter electrodes in a specified region, etc.). During the calibration process, a hand position sensor (e.g., a leap motion sensor) will be used to accurately quantify hand position and link it to each calibration pattern. This step facilitates pattern standardization.

Turning now to FIG. 9, use of the FES calibration database 140 for positioning a user's hand by FES is described. In an operation 160, the values for the set of user metrics are received. The set of user metrics received at operation 160 is suitably the same as the set of user metrics in the operation 144 already described in conjunction with the database construction of FIG. 8. The user then dons the FES device 10, and a target hand position 162 is received. For example, in a gaming, VR, or AR system, the target hand position 162 may be provided by that system. In the case of therapy for an SCI or stroke patient, the target hand position 162 may be obtained from a brain-computer interface (BCI). These are merely illustrative examples. The target hand position 162 is received as values for the same set of hand position measurements as were acquired of the reference users in the operation 150 of the database construction phase (FIG. 8).

In an operation 164, a query is formulated and applied against the FES calibration database 140. The query includes the values for the set of user metrics received at the operation 160 and the values for the set of hand position measurements received at the operation 162. By way of non-limiting illustrative example, the FES calibration database 140 may be implemented as a relational database and the query may be formulated as a SQL query. The query 164 suitably retrieves those records of the FES calibration database 140 whose user metrics fields and hand position measurements fields most closely match the user metrics received in operation 160 and the values of the hand position measurements received at the operation 162, respectively. The query 164 may optionally specify other parameters, such as a minimum and/or maximum number of "close" records to retrieve, and/or parameters defining how close a record must be to be retrieved. For example, if the set of user metrics is treated as a user metrics vector and likewise the set of hand position measurements is treated as a hand position metrics vector, then "closeness" can be quantified as follows. A user Euclidean distance (or other vector distance) is computed between the vector of the values of the set of user metrics received at the operation 160 and the vector representing the values contained in the user metrics field of the record being assessed. Likewise, a hand position Euclidean distance (or other vector distance) is computed between the vector of the values of the set of hand position measurements received at the operation 162 and the vector representing the values contained in the hand position metrics field of the record being assessed. One or both of these vector distances can further optionally have its components weighted to emphasize or deemphasize information based on importance for the specific target hand position, e.g. if the target hand position is to extend the thumb then hand position measurements quantifying the thumb position may be weighted more heavily than hand position measurements quantifying positions of the (other) fingers.

In an operation 166, the query retrieval results are combined to generate a user-specific energization pattern 168 for generating the target hand position received at the operation 162. In a straightforward approach, the energization pattern of the closest returned record is chosen as the user-specific energization pattern 168. In another approach, the energization patterns for the N closest returned records are combined (where N is an integer greater than or equal to 2) in a weighted combination using the user and hand position Euclidean distances as weights. These are merely illustrative examples. The resulting user-specific energization pattern 168 is then applied to the FES device 10 via the FES driver 22 to produce the target hand position.

Figure 10:
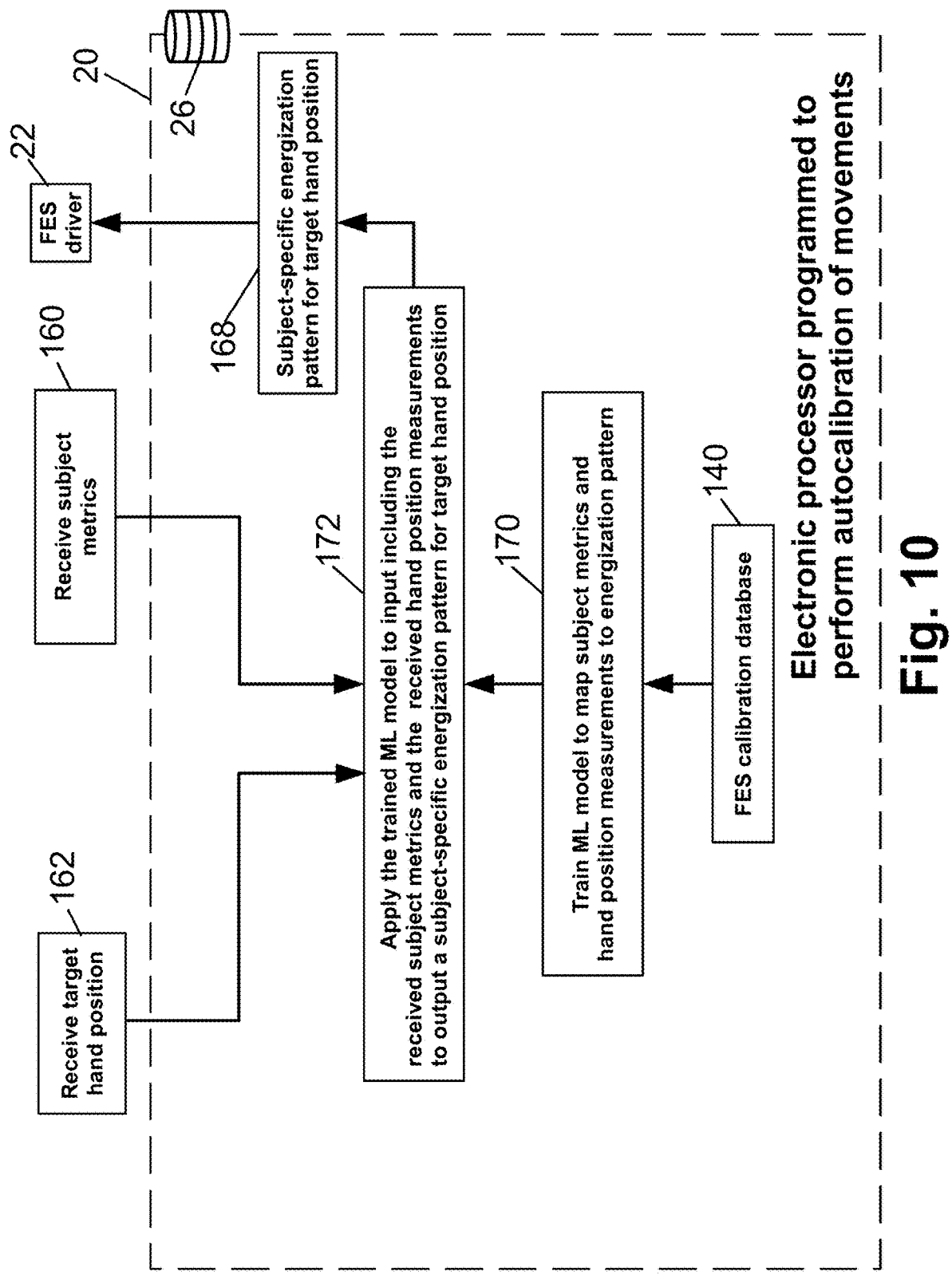

With reference to FIG. 10, in a variant embodiment the FES calibration database 140 is used in an operation 170 as training data to train a ML model such as an ANN to receive input including the user measurements and the measured hand position and to output the energization pattern. For example, backpropagation training can be used to optimize learned parameters of the ANN (e.g., weights and activation function parameters of the ANN) to output the energization pattern in response to receiving the corresponding values of the sets of user metrics and hand position measurements for the records stored in the FES calibration database 140. Instead of an ANN, the ML model may be a support vector machine (SVM), regression model, Bayesian network, or so forth. In this variant embodiment, the operations 164, 166 of FIG. 9 are replaced by an operation 172 in which the user metrics received at the operation 160 and the hand position measurements for the target hand position received at the operation 162 are input to the ANN or other ML model trained via operation 170, and the output is the user-specific energization pattern 168.

In the embodiment of FIG. 10, it will be appreciated that the ML model training operation 170 is computationally complex, especially if the FES calibration database 140 is large (i.e. contains a large number of records). In view of this, it is contemplated that the ML model training operation 170 may be performed offline, that is, by a network-based server computer, cloud computing resource, or other large-scale computing system comprising an electronic processor or set of electronic processors, and the resulting trained ML model may then be electronically transferred to the electronic processor 20 that is connected to control the FES driver 22. The electronic transfer of the ML model may for example be done over the Internet and/or another electronic network, or may be done by copying the trained ML model to a flash drive or other physical storage device that is then physically connected to the electronic processor 20. The network-based server computer, cloud computing resource, or other large-scale computing system may in some embodiments be broadly considered to be an element of the FES system.

It will be appreciated that an advantage of the approaches of FIGS. 8-10 over the approaches of FIGS. 5-7 is that the approaches of FIGS. 8-10 can be employed to enable the FES device 10 to be calibrated for, and used by, an SCI or stroke patient who cannot produce sufficient (or any) EMG signals.

A further advantage of the approach of FIGS. 8-10 is that they enable use of the FES device 10 by a user without specifically calibrating the FES device 10 for that user. Such operation without user-specific calibration is expected to be feasible if the FES calibration database 140 is sufficiently comprehensive to include reference users of suitable similarity to the user to enable accurate interpolation of the user-specific energization pattern 168. Alternatively, if the FES calibration database 140 is not sufficiently comprehensive for accurate interpolation without any user-specific calibration, then the approaches of FIGS. 8-10 are at least expected to output the user-specific energization pattern 168 for an intended movement 162 which are close to satisfactory for the user, so that the user-specific calibration of the FES device 10 is limited to fine-tuning the already close-to-satisfactory user-specific energization pattern 168.

In the foregoing, the FES device 10 is a sleeve and/or glove that is configured for connection with an associated body part, namely an arm and/or hand. More generally, the FES device may be a glove worn on a paralyzed hand, or a sleeve worn on a paralyzed arm or leg, a combination thereof, and/or so forth; in which the glove and/or sleeve or so forth has an array of electrodes disposed on the inside that contact the skin of the hand or limb on which the glove or sleeve is placed. In the generalized sense, the set of hand position measurements may more generally be a set of body part position measurements, and the target hand position is more generally a target position of the associated body part represented as values for the set of body part position measurements. The disclosed FES device and associated calibration and control may be applied for any such FES device, and may be useful in applications including (but not limited to): therapy and/or mobility assistance for impaired individuals (e.g., SCI or stroke patients); providing enhanced immersive experience in gaming, VR, and/or AR systems; and/or so forth.

In yet another variant, the iterative calibration can be speeded up by providing a method to rapidly scan the landscape of the garment safely, without having to ramp the amplitude from 0 mA (or another start value 50, see FIG. 2) for each proposal. For example, this may be performed to implement the seeding 28 in the embodiment of FIG. 1. In one approach, a current amplitude gradient is applied across the electrode array, with the amplitude scaled based on forearm or other muscular regions (e.g., higher on extensor muscles, lower on flexors, lower near wrist). This enables ROI sweeps to scan the whole sleeve at a constant ROI amplitude. Extensor muscles require more current to evoke movement relative to flexor muscle. An ROI sweep entails moving the ROI across the sleeve. For example, if the ROI is to move from left to right, then at each step of the sweep the leftmost (e.g.) one or two rows of electrodes are dropped (e.g. not energized) and a new rightmost (e.g.) one or two rows of electrodes are added (e.g. energized). This variant also advantageously enables omission of the seeding operation 28. This variant approach provides for rapidly calibrating the FES device 10 in an automated fashion to evoke target movements ab initio. Additionally, this variant method enables specific muscle groups to be targeted through modified coarse landscape sweeps of regions of interest (ROIs). The variant approach operates by performing coarse landscape sweeps of cathodic and anodic ROIs across the electrode array of the FES device 10 to determine NMES patterns that evoke movements closest to target movements. A local search algorithm can be used to optimize the NMES patterns.

Figure 11:
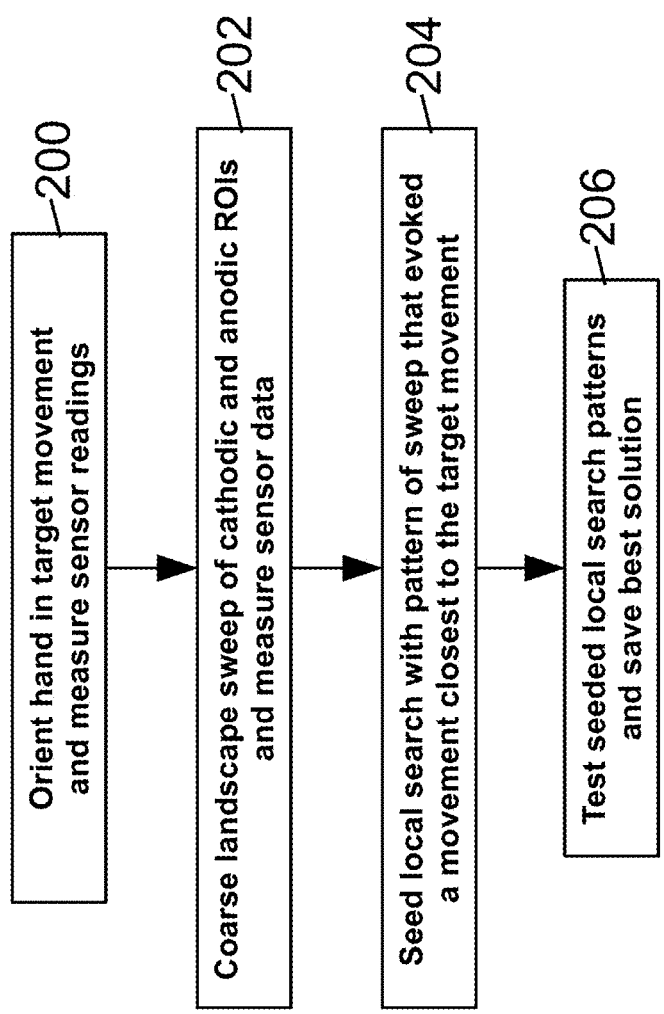
FIG. 11 diagrammatically illustrates another autocalibration approach.

With reference to FIG. 11, an illustrative embodiment of this variant approach is described. In an operation 200, for each target movement, the user first orients the hand or other associated body part in the desired position (or, if the hand or other associated body part is paralyzed then a physical therapist or other assistance orients it in the desired position) so as to implement the target movement while wearing the FES device 10 with sensors for monitoring the movement (e.g., bend sensors on each finger, and additional IMU sensors to measure hand and wrist orientation) and the sensor readings are measured and saved with annotation to the target movement.

In an operation 202, a coarse landscape sweep of cathodic and anodic ROIs is performed across the entire sleeve and glove sensor data is recorded simultaneously. For example, in order to generate a target pattern, at least one cathodic ROI (e.g., at least one cathodic region) and at least one anodic ROI (e.g., at least one anodic region) for FES may be defined. In other words, the operator may select at least one cathodic ROI and at least one anodic ROI for FES. For example, the ROI may be defined through a graphic interface provided by an FES calibration device including the electronic processor 20 of FIG. 1 and further comprising a monitor via which the graphic interface is shown. The operator may select a two-dimensional region on the graphic interface and further drag and/or resize the region to ultimately define a ROI. The graphic interface may be implemented as a FES electrode mapping which represents a mapping of virtual electrodes shown on the graphic interface to physical electrodes in the FES system. Alternatively, the ROI may be defined automatically based on the sensor readings acquired during the operation 200, for example, using the following equation:

$$M(x, y, t) = s(-x, -t_{x1}) * S(x, t_{x2}) * s(-y, -t_{y1}) * S(y, t_{y2}) \text{ where} \quad (4)$$

$$t = (t_{x1}, t_{x2}, t_{y1}, t_{y2}) \text{ and } S(x, t) = \frac{1}{1 + e^{C*(-x+t)}}$$

Here, M(x,y,t) represents the output along two dimensions—the x and y spatial locations on the FES device (e.g., FES sleeve 10); t is an array with lower and upper bound cutoffs for the regions; $t_{x1}$ is lower x bound cutoff and $t_{x2}$ is upper x bound cutoff, and similarly, $t_{y1}$ is lower y bound cutoff and $t_{y2}$ is upper y bound cutoff; S(x,t) is a sigmoid function that represents one side of the curve along a single dimension (for example x-axis). This may also be expanded to cover sharpness parameter; t is the "cutoff" value which defines where the slope of the sigmoid occurs; c is a sharpness constant which dictates how steep the slope is at the cutoff; The above-mentioned parameters are what define the boundaries of the ROI. Therefore, the ROI may be defined/obtained through Equation (4). The defined ROI may be scanned across the FES device 10 to identify functional movements. That is, the FES calibration device may scan the defined ROIs across the FES device to identify functional movements. Thus, after scanning the defined ROI across the FES device, the FES calibration device may identify functional movements from the user. Then, the FES calibration device may use the identified functional movements to update the ROI, define a new ROI and/or improve FES calibration. The updated ROI may also be defined/obtained through Equation (4). In order to generate a target pattern, at least one cathodic ROI (e.g., at least one cathodic region) and at least one anodic ROI (e.g., at least one anodic region) for FES may be defined. In other words, the operator may select at least one cathodic ROI and at least one anodic ROI for FES. The thusly defined ROI is then converted to a target pattern. The target pattern may be a two-dimensional (2D) pattern or a three-dimensional (3D) pattern. The FES calibration device may convert the ROI to a 3D target pattern using the following equation:

$$Z = \sum_{a=1}^{m} M_{(+)}(x_a, y_a, t_a) - \sum_{b=1}^{n} M_{(-)}(x_b, y_b, t_b) \quad (5)$$

where m denotes the number of cathodic ROIs, n denotes the number of anodic ROIs, and t denotes a set of thresholds for each ROI. The first half of the Equation (5) represents calculation for the cathodes, while the second half of the Equation (5) represents calculation for anodes. Since Equation (5) comprises outcome of Equation (4), which includes the sigmoid function S(x,t), the ROI may also be considered to be converted to the target pattern based on a sigmoid function. It should be noted that above exemplary sigmoid function is only given by way of example, and it's not intended to be exclusive. Any other sigmoid function may be available as long as it may help to realize the principles disclosed in this disclosure. For example, a gaussian function may be used to convert the ROI to a target pattern. In this case, the ROI may be defined in the same or similar manner as discussed above, but in some scenario, underlying parameters used to define the ROI may be different from those above. For example, the width of the ROI may define the width or standard deviation of the gaussian.

With continuing reference to FIG. 11, in an operation 204 a local search is then seeded with the pattern that evoked a movement closest to the target movement (measured in operation 200) during the landscape sweep of operation 202, based on the sensor data measured during these operations 200, 202. Mean squared error (MSE) of the sensor data between each movement evoked in operation 202 and the target movement as measured in operation 200 is used to determine the closest NMES pattern. Rather than MSE, another suitable comparison metric may be used such as the WSOS of Equation (1) or the $WSOS_{Movement}$ of Equation (2). Even after the coarse localization of ROIs, the remaining range of potential defining parameters is extremely large. To efficiently explore this parameter space, a D-optimal statistical experiment design centered around the seed calibration may optionally be used to select sets of parameters. This method minimizes autocalibration time by generating a small but diverse set of likely patterns. This statistical design samples NMES parameters near the seed calibration to fine tune the pattern. (A genetic algorithm, or similar, can be used as well to converge on a solution). In an operation 206, the new patterns are attempted, and the best pattern is saved for each target movement. Again, MSE, WSOS, or another comparison metric applied to the sensor data is used to determine closest NMES patterns.

Using the method of FIG. 11, rapid FES autocalibration from scratch was experimentally demonstrated for three movements: Middle Flexion, Hand Close, and Pinch Grip. The Middle Flexion total time for autocalibration was 45.84 seconds. The Hand Close total time for autocalibration was 51.17 seconds. The Pinch Grip total time for autocalibration was 45.30 seconds. It is noted that each of these start with the same landscape sweep that took about 32 seconds. However, in a variant approach the sweep may be run only once, so in a refinement it would take 32 seconds to run an initial landscape sweep, and then about 13-19 additional seconds for each movement. The experiments were performed using an FES glove 10 with only 5 sensors and a relatively poor fit to the hand. Improved hardware with more bend and/or IMU sensors is expected to further improve on these initial results. Sweeps can be modified to target specific muscle groups, but the coarse landscape sweep is optimal for a broad range of movements.

In a variant on the approach of FIG. 11, the operator determination of the ROIs may be automated to completely remove the operator from the autocalibration loop. In this further variant approach, the ROIs autonomously scan over the sleeve and pick the best FES patterns for each desired movement. This enables the autocalibration to be further expedited and enables it to be initiated by a non-technical user.

Figure 12:
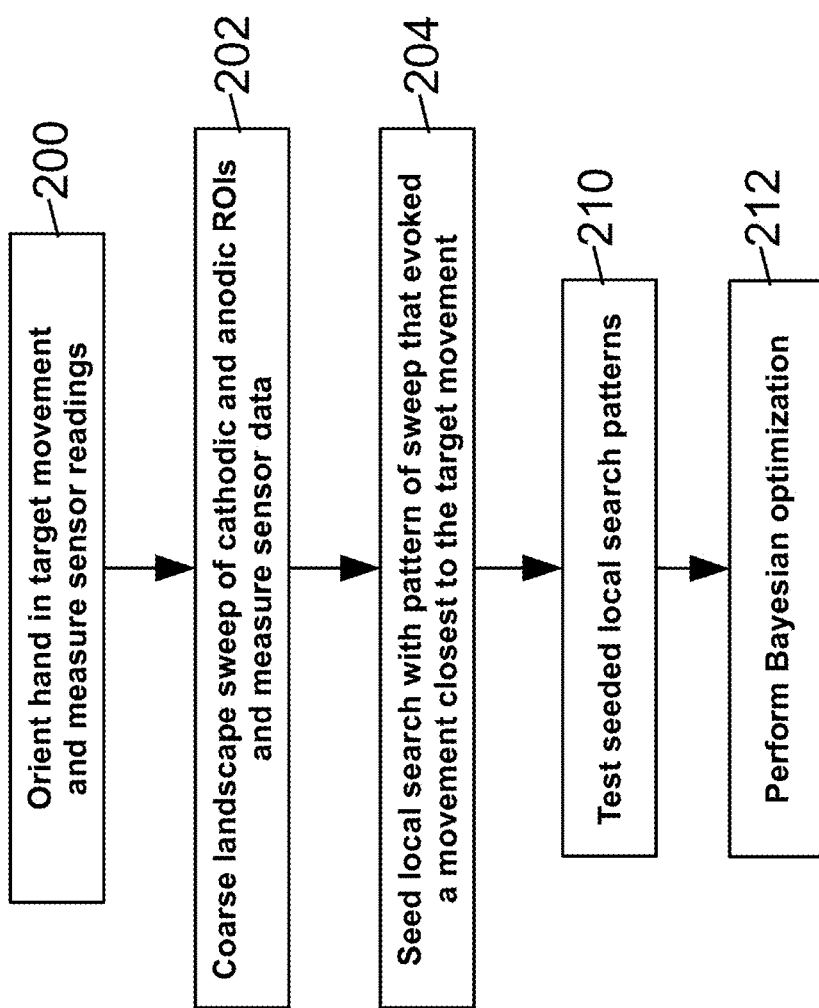
FIG. 12 diagrammatically illustrates another autocalibration approach.

With reference to FIG. 12, in this further variant approach the operations 200, 202, and 204 are performed as already described with reference to FIG. 11 to select initial patterns to test (or another algorithm is employed to select the patterns). In an operation 210 the new patterns are attempted, and sensor data acquired for each tested pattern. Again, sensor data is used to compare all the evoked movements in operation 210 against each target movement. The comparisons may use MSE of sensor readings or comparable loss function to evaluate the similarity of the evoked and target movements, as already mentioned. These observations, comprising corresponding ROI parameters and loss values, are used as seed evaluations for Bayesian optimization 212. In the Bayesian optimization 212, the seed points are used to form a prior over the objective function. For each target movement, Bayesian optimization is used to decide new ROI parameters to evaluate, the parameters are tested, and then the Bayesian prior is updated as to its belief about the objective function. This loop continues until a best pattern is calibrated for the target movement (or the user stops the procedure). The time dedicated to optimization can be varied to shift the balance between calibration time and quality of the optimized pattern for the target movement. At the end of optimization, the system saves the pattern with the lowest loss. Because both the scans and optimization do not require user-input, the calibration procedure of FIG. 12 can be fully autonomous.

Note that the ROI scans of operation 202 are not necessarily required for the Bayesian optimization 212. For example, the Bayesian optimization 212 may operate without any seed data (that is, operation 204 may optionally be omitted in FIG. 12). However, by predefining scans that are likely to evoke movements (using anatomical information, historical recordings et cetera, or using the approach of operations 202 and 204), the optimization efficiency improves. Likewise, The ROI sweep (operation 202) is also optional, and is not necessary but helps to ground the Bayesian optimization with seeded values. As an example, in the approach of FIG. 1 the generating of the updated pool of proposals for the next iteration 38 may comprise performing Bayesian optimization of the proposals of the current pool of proposals.

In the foregoing embodiments, the assessment of how well a pattern matches a target movement relies upon having measurements of the target movement, e.g. the target sensor positions $T_i$ of the WSOS of Equation (1) or corresponding data collected in operation 200 of the approaches of FIGS. 5 and 6.

With reference to FIG. 13, in yet another variant approach, electromyography (EMG) signals from electrodes 220 of the FES device 10 (shown in FIG. 13 in an "unrolled" pattern where the horizontal axis is the position x along the arm and the vertical axis it the unrolled angle ϕ around the arm) corresponding to mapped to muscle anatomy (e.g. an three illustrative muscles 222, 224, 226) can be used as an electrodes-to-muscle anatomy mapping to determine which muscles are responsible for which movements, then that electrode information can be used to stimulate the appropriate muscles, for example as defined by cathode and anode ROIs 228. That is, EMG signals are used to instruct which electrodes 220 are needed for FES to evoke that same movement. In one contemplated approach, the electrodes receiving EMG signals are used to directly map which electrodes to use for a given motion. In another contemplated approach, the underlying musculature anatomy of the arm (or other body part) is used to determine which muscles are being activated (with or without motion evoked), and that information as to which muscles are being used is leveraged to create the pattern of FES electrodes needed to evoke the motion based on known anatomy.

This approach using EMG signals for the calibration may improve calibration speed, as no motion is required to determine which FES electrodes are needed for a particular motion. The user need only trigger EMG (in the absence or presence of motion in the muscles) to provide the correct anatomical locations for FES electrodes. Furthermore, some cases in which the body part being energized by FES is paralyzed but some EMG signals are still being generated (albeit with insufficient strength to evoke movement of the body part), the autocalibration can be performed without the need for a physical therapist or other assistant to move the body part into the target movement, or for the user to employ (for example) an able other hand to do so. Additionally, no FES device or camera is needed to learn the evoked motion—rather the system itself captures the electrode map directly for every motion.

Notably, the muscle mapping of the embodiment of FIG. 13 is readily incorporated into the approach described with reference to FIG. 5, which relies upon the EMG signals readout 100 detecting electromyography (EMG) signals generated by the muscles themselves in response to the user 12 willing the intended movement. Knowledge of the mapping of electrodes to the underlying musculature anatomy can expedite the approach of FIG. 5 and improve its accuracy.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A functional electrical stimulation (FES) system comprising:
   a garment having an array of electrodes arranged to contact the skin of a body part to be energized by FES when the garment is worn on the body part; and
   an electronic processor programmed to perform FES calibration including:
      determining parameter values of a stimulation pattern for causing a desired movement of the body part, wherein the stimulation pattern includes at least two parameterized bivariate Gaussian distributions over a group of the electrodes; and
      energizing the electrodes of the garment in accordance with the stimulation pattern having the determined parameter values to cause the desired movement of the body part.

2. The FES system of claim 1, wherein the parameters of each of the two parameterized bivariate Gaussian distributions include two means, and the determining of the parameter values of the stimulation pattern includes determining parameter values for the two means of each of the two parameterized bivariate Gaussian distributions.

3. The FES system of claim 1, wherein the parameters of each of the two parameterized bivariate Gaussian distributions include two means and three variances, and the determining of the parameter values of the stimulation pattern includes determining parameter values for the two means and three variances of each of the two parameterized bivariate Gaussian distributions.

4. The FES system of claim 3, wherein the determining of the parameter values of the stimulation pattern further includes determining an amplitude of the stimulation pattern.

5. The FES system of claim 2, wherein the parameters of each of the two parameterized bivariate Gaussian distributions include two means and the parameters of each of the two parameterized bivariate Gaussian distributions do not include any variances, and the determining of the parameter values of the stimulation pattern includes determining parameter values for the two means of each of the two parameterized bivariate Gaussian distributions.

6. The FES system of claim 5, wherein the determining of the parameter values of the stimulation pattern further includes determining an amplitude of the stimulation pattern.

7. A functional electrical stimulation (FES) system comprising:
   a garment having an array of electrodes arranged to contact the skin of a body part to be energized by FES when the garment is worn on the body part; and an electronic processor programmed to perform FES calibration including:
    determining parameter values of a stimulation pattern for causing a desired movement of the body part, wherein the stimulation pattern includes at least one parameterized distribution over a group of the electrodes and wherein the determining of the parameter values of the stimulation pattern includes determining no more than eleven parameter values of the stimulation pattern; and
    energizing the electrodes of the garment in accordance with the stimulation pattern having the determined parameter values to cause the desired movement of the body part.

8. The FES system of claim 7, wherein the determining of the parameter values of the stimulation pattern includes determining no more than six parameter values of the stimulation pattern.

9. A functional electrical stimulation (FES) system comprising:
    a garment having an array of electrodes arranged to contact the skin of a body part to be energized by FES when the garment is worn on the body part;
    sensors for measuring a position of the body part; and
    an electronic processor programmed to perform an FES calibration including:
        during the moving of the body part to a target position and using the sensors, acquiring target sensor data measuring the moving;
        performing a sweep of cathodic and anodic regions of interest (ROIs) over the array of electrodes to evoke FES of the body part and, during the sweep and using the sensors, acquiring sweep sensor data measuring movements of the body part evoked by energization of the cathodic and anodic ROIs during the sweep;
        comparing the sweep sensor data and the target sensor data to identify one or more seed energization patterns of the electrodes applied during the sweep that evoked a movement of the body part closest to the target movement;
        performing a local search of energization patterns around each seed energization pattern;
        during the local search and using the sensors, acquiring local search sensor data measuring movements of the body part evoked by energization patterns of the local search; and
        determining an optimal energization pattern for applying FES to evoke movement of the body part to the target position by comparing the local search sensor data and the target sensor data;
    wherein at least one of:
        the local search is performed using Bayesian optimization with the one or more seed energization patterns forming a prior over an objective function of the Bayesian optimization; and/or
        the sweep and the local search are performed autonomously without user input.

10. The FES system of claim 9, wherein the local search is performed using a genetic algorithm.

11. The FES system of claim 9, wherein the local search is performed using Bayesian optimization with the one or more seed energization patterns forming a prior over an objective function of the Bayesian optimization.

12. The FES system of claim 9, wherein the sweep and the local search are performed autonomously without user input.

13. A functional electrical stimulation (FES) system comprising:
    a garment having an array of electrodes arranged to contact the skin of a body part to be energized by FES when the garment is worn on the body part;
    sensors for measuring a position of the body part, wherein the sensors comprise bend sensors and/or inertial measurement unit (IMU) sensors; and
    an electronic processor programmed to perform an FES calibration including:
        during the moving of the body part to a target position and using the sensors, acquiring target sensor data measuring the moving;
        performing a sweep of cathodic and anodic regions of interest (ROIs) over the array of electrodes to evoke FES of the body part and, during the sweep and using the sensors, acquiring sweep sensor data measuring movements of the body part evoked by energization of the cathodic and anodic ROIs during the sweep; and
        comparing the sweep sensor data and the target sensor data to identify one or more seed energization patterns of the electrodes applied during the sweep that evoked a movement of the body part closest to the target movement.

14. A functional electrical stimulation (FES) system comprising:
    a garment having an array of electrodes arranged to contact the skin of a body part to be energized by FES when the garment is worn on the body part;
    sensors for measuring a position of the body part; and
    an electronic processor programmed to perform an FES calibration including:
        during the moving of the body part to a target position and using the sensors, acquiring target sensor data measuring the moving;
        performing a sweep of cathodic and anodic regions of interest (ROIs) over the array of electrodes to evoke FES of the body part, wherein the sweep includes converting the cathodic and anodic ROIs to energization patterns;
        during the sweep and using the sensors, acquiring sweep sensor data measuring movements of the body part evoked by energization of the cathodic and anodic ROIs during the sweep; and
        comparing the sweep sensor data and the target sensor data to identify one or more seed energization patterns of the electrodes applied during the sweep that evoked a movement of the body part closest to the target movement.

\* \* \* \* \*